US010265335B2

(12) United States Patent
Paus et al.

(10) Patent No.: US 10,265,335 B2
(45) Date of Patent: Apr. 23, 2019

(54) USE OF NON-DIGESTIBLE OLIGOSACCHARIDES

(75) Inventors: Ralf Ludwig Paus, Hamburg (DE); Catherine Anne O'Neill, Burnedge (GB)

(73) Assignee: Curapel (Scotland) Limited, Glasgow (GB)

( * ) Notice: Subject to any disclaimer, the term of this patent is extended or adjusted under 35 U.S.C. 154(b) by 0 days.

(21) Appl. No.: 13/393,948

(22) PCT Filed: Sep. 3, 2010

(86) PCT No.: PCT/GB2010/001680
§ 371 (c)(1),
(2), (4) Date: Mar. 2, 2012

(87) PCT Pub. No.: WO2011/027128
PCT Pub. Date: Mar. 10, 2011

(65) Prior Publication Data
US 2012/0190641 A1 Jul. 26, 2012

(30) Foreign Application Priority Data
Sep. 3, 2009 (GB) .................................. 0915315.6

(51) Int. Cl.
| | |
|---|---|
| *A61K 9/00* | (2006.01) |
| *A61K 9/20* | (2006.01) |
| *A61K 31/702* | (2006.01) |
| *A23L 33/21* | (2016.01) |
| *A61K 47/06* | (2006.01) |
| *A61K 47/10* | (2017.01) |

(52) U.S. Cl.
CPC ............ *A61K 31/702* (2013.01); *A23L 33/21* (2016.08); *A61K 9/0014* (2013.01); *A61K 9/0095* (2013.01); *A23V 2002/00* (2013.01); *A61K 9/2018* (2013.01); *A61K 47/06* (2013.01); *A61K 47/10* (2013.01)

(58) Field of Classification Search
CPC .. A61K 31/702; A61K 9/0014; A61K 9/0095; A23L 1/308
See application file for complete search history.

(56) References Cited

U.S. PATENT DOCUMENTS

| | | | |
|---|---|---|---|
| 3,472,931 A | 10/1969 | Stoughton et al. | |
| 3,891,757 A | 6/1975 | Higuchi | |
| 4,613,377 A * | 9/1986 | Yamazaki | C13K 11/00 127/39 |
| 5,614,202 A | 3/1997 | DeFina | |
| 5,721,345 A | 2/1998 | Roberfroid et al. | |
| 5,994,326 A | 11/1999 | Matsuda et al. | |
| 6,143,730 A | 11/2000 | Parish et al. | |
| 6,946,121 B2 | 9/2005 | Martinez et al. | |
| 2003/0045505 A1 | 3/2003 | Martinez et al. | |
| 2004/0062758 A1 * | 4/2004 | Mayra-Makinen et al. | 424/93.45 |
| 2006/0165670 A1 | 7/2006 | Beer et al. | |
| 2007/0065386 A1 | 3/2007 | Lubrano et al. | |
| 2009/0163427 A1 | 6/2009 | Dikovskiy | |

FOREIGN PATENT DOCUMENTS

| | | | |
|---|---|---|---|
| DE | 202006017823 U1 | 2/2007 | |
| GB | 1001949 | 8/1965 | |
| GB | 1464975 | 2/1977 | |
| JP | 57055620 | 4/1982 | |
| JP | 10072312 | 3/1998 | |
| JP | 2003137790 A | 5/2003 | |
| JP | 2006509797 A | 3/2006 | |
| WO | 9804270 A1 | 2/1998 | |
| WO | 0006115 A1 | 2/2000 | |
| WO | 2004/000045 | 12/2003 | |
| WO | 2004000045 A2 | 12/2003 | |
| WO | 2004052121 A1 | 6/2004 | |
| WO | WO 2005/030230 A1 * | 7/2005 | ............ A61K 35/74 |
| WO | WO 2010/000578 * | 1/2010 | |
| WO | 2011027128 A1 | 3/2011 | |

OTHER PUBLICATIONS

Niness, K.R. (1999) Inulin and Oligofructose: What Are They? Journal of Nutrition, vol. 129, p. 1402S-1406S.*
Ando, H.Y. and Radebaugh, G.W. (2000) "Preformulation" in Remington: The Science and Practice of Pharmacy, 20th Edition. Edited by Alfonso R. Gennaro. p. 704-712.*
Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"What is psoriasis?" from Psoriasis Connections [online], [Retrieved on Jun. 30, 2011]. Retrieved from the internet <http://www.psoriasisconnect.com/learn/what-is-psoriasis.jsp>.*
Machine translation of JP10-072312 (1998) [online] [Retrieved Dec. 28, 2014] Retrieved from the internet at <http://dossier1.ipdl.inpit.go.jp/AIPN/odse_top_dn.ipdl?N0000=7400>.*
Roberfroid, M.B., Van Loo, J.A.E., Gibson, G.R. (1998) The Bifidogenic Nature of Chicory Inulin and Its Hydrolysis Products. The Journal of Nutrition, vol. 128, p. 11-19.*
Gibson, G.R., Rabiu, B., Rycroft, C.E., Rastall, R.A. (2003) "Trans-Galactooligosaccharides as Prebiotics" in Handbook of Functional Dairy Products. Edited by Colette Shortt and John O'Brien, published by CRC Press, p. 91-108.*
Le Leu, R.K., Brown, I.L., Hu, Y., Bird, A.R., Jackson, M., Esterman, A., Young, G.P. (2005) A Synbiotic Combination of Resistant Starch and Bifidobacterium lactis Facilitates Apoptotic Deletion of Carcinogen-Damaged Cells in Rat Colon. The Journal of Nutrition, vol. 135, p. 996-1001.*

(Continued)

*Primary Examiner* — Leigh C Maier
(74) *Attorney, Agent, or Firm* — Conley Rose, P.C.; Rodney B. Carroll

(57) ABSTRACT

Use of a non-digestible oligosaccharide or salt thereof for producing an anti proliferative effect in a subject wherein the non-digestible oligosaccharide is of formulae (i) [A]-[B]$_n$ Formula 1 wherein A and B are each independently a five or six membered saccharide unit and n is 2 to 10.

10 Claims, 6 Drawing Sheets

(56) References Cited

OTHER PUBLICATIONS

Marnewick et al "Inhibition of tumour promotion in mouse skins . . . " Cancer Lett. vol. 224, pp. 193-202. (Year: 2005).*
Sporn, M.B. et al. Proliferative Diseases. Am. J. Med., vol. 70, No. 6. Jun. 1981. pp. 1231-1236.
English-language abstract of JP 10-072312 dated Mar. 17, 1998.
English-language abstract of published PCT application WO 01/38399 published May 31, 2001.
English-language abstract of JP 2007-106724 dated Apr. 26, 2007.
Munjal, U. et al. Fermentation products of inulin-type fructans reduce proliferation and induce apoptosis in human colon tumour cells of different stages of carcinogenesis. British Journal of Nutrition. vol. 102, No. 5. pp. 663-671, Sep. 2009.
International Search Report dated Dec. 11, 2010 in International Patent Application Serial No. PCT/GB2010/001680.
Abrams, Steven A., et al., "A combination of prebiotic short- and long-chain inulin-type fructans enhances calcium absorption and bone mineralization in young adolescents," The American Journal of Clinical Nutrition, 2005, pp. 471-476, vol. 82, American Society for Clinical Nutrition, USA.
Al-Daraji, Wael I., et al., "Modulation of NFAT-5, an outlying member of the NFAT family, in human keratinocytes and skin," Am J Transl Res, 2009, pp. 184-202, vol. 1, No. 2.
Csanadi, ZS., et al., "Production of short chain fructooligosaccharides," Hungarian Journal of Industrial Chemistry, 2008, pp. 23-26, vol. 36, No. 1-2.
Gavrieli, Yael, et al., "Identification of programmed cell death in situ via specific labeling of nuclear DNA fragmentation," The Journal of Cell Biology, Nov. 1, 1992, pp. 493-501, vol. 119, No. 3, The Rockefeller University Press.
Foreign communication from a related counterpart application—European Exam Report, EP 10 759 693.4-1460, dated May 16, 2014, 3 pages.
Foreign communication from a related counterpart application—Japanese Exam Report, JP 2012-527382, dated Sep. 30, 2014, with English translation, 11 pages.

Psoriant, 2007, Jaargang 25 maart-april-mei 2007, URL, http://www.psoriasis-v1.be/img/docs/01_2007.pdf—from Japanese Exam Report, JP 2012-527382, dated Sep. 30, 2014, 36 pages.
Katz, Martin, et al.; Scholtz-Dumas psoriasis small plaque bioassay; Journal of Dermatological Treatment, 2000, vol. 11, pp. 15-19.
Mineo, Hitoshi, et al.; Indigestible disaccharides open tight junctions and enhance net calcium, magnesium, and zinc absorption in isolated rat small and large intestinal epithelium; Digestive Diseases and Sciences, Jan. 2004, vol. 49, No. 1, pp. 122-132.
El-Gawad, A., et al., "Inhibitory effect of yoghurt and soya yoghurt containing bifidobacteria on the proliferation of Ehrlich ascites tumour cells in vitro and in vivo in a mouse tumour model," British Journal of Nutrition, 2004, pp. 81-86 vol. 92.
Kahouli, I., et al., "Design and validation of an orally administered active L. fermentum-L. acidophilus probiotic formulation using colorectal cancer ApcMin/+ mouse model," Applied Microbiology and Biotechnology, Nov. 11, 2016, 21 pages, Springer.
Kahouli, I., et al., "In-Vitro Characterization of the Anti-Cancer Activity of th Probiotic Bacterium Lactobaillus Fermentum NCIMB 5221 and Potential against Colorectal cancer Cells," Jouranl of Cancer Science and Therapy, 2015, pp. 224-235, vol. 7, No. 7, Journal of Cancer Science and Therapy.
Tiptiri-Kourpeti, A., et al., "Lactobacillus casei Exerts Anti-Proliferative Effects Accompanied by Apoptotic Cell Death and Up-Regulation of TRAIL in Colon Carcinoma Cells," PLOS ONE, Feb. 6, 2016, 20 pages.
Lee, D., et al., "Anti-proliferative effects of Bifidobacterium adolescentis SPM0212 extract on human colon cancer cell lines," BioMed Central, Oct. 27, 2008, 8 pages, Lee et al; Licensee: BioMed Central Ltd.
Wang, S., et al., "Screening for Antiproliferative Effect on Lactobacillus Strains Against Colon Cancer HT-29 Cells," Advanced Materials Research, 2012, pp. 1039-1043, vol. 573-574, Trans Tech Publications, Switzerland.
Magcwebeba, Tandeka U., et al., "In Vitro Chemopreventive Properties of Green Tea, Rooibos and Honeybush Extracts in Skin Cells," Molecules, 2016, 18 pages, vol. 21, No. 1622, MDPI.

* cited by examiner

USE OF NON-DIGESTIBLE OLIGOSACCHARIDES

The present invention relates to a non-digestible oligosaccharide for use in producing an anti-proliferative effect in a subject. More particularly the present invention relates to a non-digestible oligosaccharide for use in inhibiting hyper-proliferation in a subject, nutritional products comprising same and pharmaceutical preparations thereof.

Non-digestible oligosaccharides are well known and are an inert part of the fibre component of the diet. They are naturally occurring and are found in the edible parts of plants such as garlic, onions, asparagus, artichoke and chicory. More specifically, non-digestible oligosaccharides are low molecular weight carbohydrates consisting of sugar moieties that resist hydrolysis in the gastrointestinal tract by virtue of the β-configuration of their glycosidic bond. In the colon, degradation by bacterial enzymes can produce water and short chain fatty acids that are believed to have positive health benefits. Additionally, some non-digestible oligosaccharides are actively prebiotic, that is they stimulate the growth of so called "friendly bacteria".

Non-digestible oligosaccharides are extensively used in the food industry in prebiotic formulations to stimulate the growth or activity of bacteria in the digestive system that are believed to be beneficial to the health of a subject.

The present inventors have now appreciated that, as well as their prebiotic properties, non-digestible oligosaccharides have anti-proliferative properties, that is, they are effective in producing an anti-proliferative effect. More specifically, the present inventors have now identified that non-digestible oligosaccharides can specifically target keratinocytes and importantly can inhibit the hyper-proliferation characteristic of psoriatic skin.

There are several types of psoriasis, the most common being plaque psoriasis, which causes red scaly patches (psoriatic plaques) to appear on the skin that represent areas of inflammation and excessive skin production. Other types include flexural, guttate, pustular, inverse, nail, erythrodermic psoriasis and psoriatic arthritis. The different types of psoriasis vary by degree of severity based on the amount of body surface area covered by lesions (ranging for example from mild with less that 2%; to moderate ranging from 3% to 10%; and to severe based on greater than 10% of total body surface coverage).

The causes of skin diseases such as psoriasis are not well understood and it is believed that numerous factors are involved. These factors are believed to include defects in the process by which skin cells of subjects grow, reproduce and differentiate, as well as immune-mediated processes (that is, abnormal immune responses). One cause of psoriasis is believed to be an abnormally high rate of epidermal skin cell growth. Normal skin cells grow in a twenty eight-day cycle, whereas in psoriasis the cycle is drastically reduced to between three and six days. This results in new skin cells reaching the surface at a rate five times faster than normal and manifests itself in outbreaks of scaly red patches of skin. Additionally, psoriatic skin is characterised by long-lived keratinocytes that further compound the raised scaly nature of the disease.

Psoriasis profoundly affects a sufferer's quality of life and social functioning and there is an urgent need for effective therapies. Prevalence is high, affecting between 1 to 3% of the world's population or approximately sixteen million individuals.

Psoriasis currently is managed by drug therapy and/or by exposure to ultraviolet radiation. However, there is a low level of therapeutic penetration in psoriasis, partly as a consequence of poor treatment efficacy, poor therapeutic safety, treatment cost and low levels of patient compliance as a result of frustrations with existing therapy approaches. Thus, skin disorders such as psoriasis can be debilitating and cause anxiety, loss of quality of life, and depression in sufferers. Such skin disorders often reoccur after conventional treatments, making their long-term management and treatment difficult. Skin disorders such as psoriasis therefore represent a major problem to sufferers and effective treatments are urgently required, especially effective treatments that exhibit low toxicity and side effects. However, the numerous factors involved make providing such an effective treatment difficult and challenging to persons skilled in the art.

US-2007/0065386 discloses the use of oligogalacturonides for stimulating differentiation of skin cells, mainly epidermal and particularly keratinocytes. There is no disclosure in this document of the use of non-digestible oligosaccharides for producing an anti-proliferative effect.

US-2003/0045505 (Martinez et al) discloses a cosmetic or dermatological external topical composition containing oligosaccharides to block immune cell ctivetaion. There is no disclosure in this document of a composition comprising a non-digestible oligosaccharide.

WO 00/06115 (Anderson et al.) describes in contrast to the present invention the use of sialyl oligosaccharides and derivatives thereof for regulating inflammatory responses and treating inflamed skin. Also described herein are topical pharmaceutical and cosmetic compositions containing such oligosaccharides and to methods of their use.

WO 98/04270 (Robert et al.) discloses the use of at least one oligosaccharide comprising 2 to 6 oside residues and having a galactose residue in the non-reducing terminal position, or a derivative of such an oligosaccharide substituted by a hydrophobic residue, for the preparation of an immunomodulating medicament. Also disclosed are a dermato-cosmetic compositions and a cosmetic treatment of hyperactive skins.

U.S. Pat. No. 5,994,326 (Masuda et al.) describes an anti-atopic dermatitis composition containing raffinose as the effective ingredient for the long term treatment of babies and infants.

In DE 20 2006 017 823 US there is disclosed a dietic food with an increased effect of free radical binder which comprises a protein and a sugar, wherein the free-radical binding effect of the food is at least 50% higher than the free radical binding effect of the food containing protein and/or sugar. The dietic food is useful for the treatment of allergic conditions such as for example neurodermatitis, acne and psoriasis and useful as a dietary supplement in cancer disease. However, there is no mention of the dietic food having an antiproliferative effect.

In JP 57055620 A (Watanabe) there is described a carcinostatic drug containing melibiose extracted from for example the root and stem of cotton plants, which can provide a completely non-toxic carcinostatic agent which can be administered continuously without side effects.

JP 2003 137790 A (MIE KARIYOU KK) discloses an agent for improving and/or preventing reduction of immuno function which comprises a fructo-oligosaccharide containing (beta)-2,1 chain coupled with a fructose oligomer as an active ingredient Finally, as background to the present invention there is described in the American Journal of Translational Research vol. 1(2), 2009, pages 184-202 by Al-Daraji et al., the modulation of NFAT-5, and outlying member of the NFAT family in human keratinocytes and skin which demonstrate for the first time expression of NFAT-5/TonEPB mRNA protein in cultured keratinocytes.

The present invention therefore seeks to address the problems outlined above in relation to the treatment of psorisis.

In contrast to the prior art the present invention provides a non-digestible oligosaccharide for use in producing an anti-proliferative effect in a subject. The anti-proliferative effect may be an anti-hyper-proliferative effect, that is it may comprise inhibition of hyper-proliferation in the subject. Thus, the present invention provides a non-digestible oligosaccharide for use in inhibiting hyper-proliferation in a subject. The hyper-proliferation may be epidermal hyper-proliferation in the subject. Thus, the present invention provides a non-digestible oligosaccharide for use in inhibiting epidermal hyper-proliferation in a subject. The hyper-proliferation may be keratinocyte hyper-proliferation in the subject. Thus, the present invention provides a non-digestible oligosaccharide for use in inhibiting keratinocyte hyper-proliferation in a subject.

There is also provided the use of a non-digestible oligosaccharide in the manufacture of a medicament for producing an anti-proliferative effect in a subject. The anti-proliferative effect may be an anti-hyperproliferative effect, that is it may comprise inhibition of hyper-proliferation in the subject. Thus, the present invention provides the use of a non-digestible oligosaccharide in the manufacture of a medicament for inhibiting hyper-proliferation in a subject. The hyper-proliferation may be epidermal hyper-proliferation in the subject. Thus, the present invention provides the use of a non-digestible oligosaccharide in the manufacture of a medicament for inhibiting epidermal hyper-proliferation in a subject. The hyper-proliferation may be keratinocyte hyper-proliferation in the subject. Thus, the present invention provides the use of a non-digestible oligosaccharide in the manufacture of a medicament for inhibiting keratinocyte hyper-proliferation in a subject.

There is also provided a method for producing an anti-proliferative effect in a subject in need thereof, which method comprises administering to said subject a therapeutically effective amount of a non-digestible oligosaccharide. The anti-proliferative effect may be an anti-hyperproliferative effect, that is it may comprise inhibition of hyper-proliferation in the subject. Thus, the present invention provides a method for inhibiting hyper-proliferation in a subject in need thereof, which method comprises administering to said subject a therapeutically effective amount of a non-digestible oligosaccharide. The hyper-proliferation may be epidermal hyper-proliferation in the subject. Thus, the present invention provides a method for inhibiting epidermal hyper-proliferation in a subject in need thereof, which method comprises administering to said subject a therapeutically effective amount of a non-digestible oligosaccharide. The hyper-proliferation may be keratinocyte hyper-proliferation in the subject. Thus, the present invention provides a method for inhibiting keratinocyte hyper-proliferation in a subject in need thereof, which method comprises administering to said subject a therapeutically effective amount of a non-digestible oligosaccharide.

According to the present invention, there is provided a non-digestible oligosaccharide as an anti-proliferative agent. There may further be provided an anti-proliferative agent comprising or consisting of a non-digestible oligosaccharide.

Without wishing to be bound by any theory, the present inventors have appreciated that non-digestible oligosaccharides, for example as currently used in the food industry, may stimulate gut function and consequently facilitate their own dose dependant gut absorption from where they can in principle access and influence other organs. The present inventors have appreciated that the stimulation of gut function by non-digestible oligosaccharides may be due to their ability to induce mineral ion (for example calcium and magnesium ion) gut absorption by opening epithelial tight junctions. For example, the non-digestible oligosaccharides oligofructose, raffinose and melibiose are known to induce mineral ion gut absorption by opening epithelial tight junctions (see, for example, Mineo H, Amano M, Chiji H, Shigematsu N, Tomita F, Hara H., Dig Dis Sci. (1):122-32., 2004). The present inventors have shown that the digestible sugar sucrose does not show such an effect. Additionally the present inventors have appreciated that non-digestible oligosaccharides may directly modify cellular functions in the skin, for example in the epidermis, especially in keratinocytes. Such properties of the non-digestible oligosaccharides have not previously been disclosed or suggested.

The epidermis is the outermost layer of the skin and is composed of four cell types and four to five layers depending on the region of the skin being considered. The four cell types are keratinocytes, melanocytes, Langerhans cells and Merkels cells. Keratinocytes are the major constituent of the epidermis, constituting about ninety five percent (95%) of the epidermis. The five layers in descending order are the stratum corneum, stratum lucidum, stratum granulosum, stratum spinosum and stratum basale. Cell division/proliferation in the basal layer maintains the epidermis.

One characteristic of skin disorders such as psoriasis is believed to be uncontrolled epidermal hyper-proliferation, primarily uncontrolled keratinocyte hyper-proliferation. In psoriasis, it is believed that the balance between keratinocyte proliferation and differentiation is disturbed, such that the skin enters a hyper-proliferative, pathogenic state. Without wishing to be bound by any theory, the present inventors believe that non-digestible oligosaccharides, such as oligofructose, can inhibit epidermal, especially keratinocyte, hyper-proliferation and therefore act as a therapy in psoriasis. In other words, it is believed that non-digestible oligosaccharides may target psoriasis by slowing the rate of keratinocyte proliferation to levels resembling non-disease or to levels equivalent to normal skin.

The use of non-digestible oligosaccharides in such therapy is advantageous because the safety profiles of non-digestible oligosaccharides are well established and as such are believed to provide safe, well-tolerated and easy to use treatments. Furthermore, the use of non-digestible oligosaccharides in such therapy is less costly than alternative therapies.

According to another aspect of the present invention, there is provided a non-digestible oligosaccharide for use in the prevention and/or treatment of a proliferative disorder of a subject. There is also provided the use of a non-digestible oligosaccharide in the manufacture of a medicament for use in the prevention and/or treatment of a proliferative disorder of a subject.

According to another aspect of the present invention, there is provided a method for the prevention and/or treatment of a proliferative disorder of a subject in need thereof, which method comprises administering to said subject a therapeutically effective amount of a non-digestible oligosaccharide.

According to another aspect of the present invention, there is provided a non-digestible oligosaccharide for use in the prevention and/or treatment of a hyper-proliferative disorder of a subject. There is also provided the use of a non-digestible oligosaccharide in the manufacture of a medicament for use in the prevention and/or treatment of a hyper-proliferative disorder of a subject.

According to another aspect of the present invention, there is provided a method for the prevention and/or treatment of a hyper-proliferative disorder of a subject in need thereof, which method comprises administering to said subject a therapeutically effective amount of a non-digestible oligosaccharide.

References herein to producing an anti-proliferative effect relate to inhibiting or suppressing cellular proliferation (that is growth and multiplication of cells) and include partial or total inhibition of cellular growth as well as decreases in the rate of proliferation or growth of cells.

Hyper-proliferation means an abnormally high rate of cell growth and multiplication, that is which results in the cells proliferating more rapidly than is normal. References herein to inhibiting hyper-proliferation therefore relate to inhibiting or suppressing the abnormally high rate of cell growth and multiplication caused by hyper-proliferation and include partial or total inhibition as well as decreases in the rate of proliferation or growth of cells.

Epidermal hyper-proliferation means an abnormally high rate of epidermal cell growth and multiplication, that is which results in the epidermal cells proliferating more rapidly than is normal. Keratinocyte hyper-proliferation means an abnormally high rate of growth and multiplication of keratinocytes, that is which results in the keratinocytes proliferating more rapidly than is normal.

Whilst not being bound to any particular theory the applicants believe that the mechanism of the present invention may reside in increased apoptosis of the cells rather than decreased proliferation, that is programmed cell death which occurs in a controlled and regulated manner in healthy organisms.

An anti-proliferative agent is a compound that can inhibit or suppress cellular proliferation (that is the growth and multiplication of cells).

References herein to proliferative disorders relate to any disorder or disease that is caused by or results from cellular proliferation, for example that is caused by or results from hypo-proliferation or hyper-proliferation. By hypo-proliferation we mean lower cellular proliferation compared to normal cellular proliferation in a subject. By hyper-proliferation we mean excessive cellular proliferation compared to normal cellular proliferation in a subject. Excessive cellular proliferation means that cells proliferate more rapidly than normal tissue growth in a subject, that is that cells proliferate at an accelerated rate. In particular, the proliferative disorder is any disorder or disease that is caused by or results from cellular hyper-proliferation.

References herein to hyper-proliferative disorders relate to any disorder or disease that is caused by or results from excessive cellular proliferation compared to normal cellular proliferation in a subject, that is, that is caused by or results from uncontrolled, autonomous cell growth.

The proliferative, particularly hyper-proliferative, disorder may be any disorder where proliferation, particularly hyper-proliferation, is evident. In particular, the proliferative, particularly hyper-proliferative, disorder may be any disorder where cellular proliferation, particularly cellular hyper-proliferation, is evident.

The proliferative, particularly hyper-proliferative, disorder may be a skin disorder. For example, the skin disorder may be psoriasis. References to psoriasis include for example all types of psoriasis unless otherwise specified. For example, references to psoriasis include plaque, flexural, guttate, pustular, nail, photosensitive, inverse and erythrodermic psoriasis and psoriatic arthritis In particular, the skin disorder may be plaque psoriasis.

The proliferative, particularly hyper-proliferative, disorder may be a disorder caused by hair follicle proliferation, particularly caused by hair follicle hyper-proliferation, for example hirsutism. Hirsutism is a disorder characterised by excess growth of hair in a masculine distribution in women.

Therefore in accordance with a first aspect of the present invention there is provided the use of a non-digestible oligosaccharide or salt thereof for producing an anti-proliferative effect in a subject wherein the non-digestible oligosaccharide is of formula (i)

$$[A]\text{-}[B]_n \qquad \text{Formula 1}$$

wherein
A and B are each independently a five or six membered saccharide unit and
n is 2 to 10.

The use of a non-digestible oligosaccharide according to the first aspect of the present invention may also be applied to inhibiting hyper-proliferation such that the non-digestible oligosaccharide is further capable of inhibiting hyper-proliferation in a subject. In this regard the hyper-proliferation is epidermal hyper-proliferation in the subject.

When the non-digestible oligosaccharide is used for inhibiting hyper-proliferation it is preferred that the hyper-proliferation is keratinocyte hyper-proliferation in the subject.

The use of a non-digestible oligosaccharide according to a first aspect of the present invention may be directed to the preparation of a medicament for the prevention and/or treatment of a proliferative disorder of a subject. More specifically, the use of a non-digestible oligosaccharide according to a first aspect of the present invention may be directed to the preparation of a medicament for the prevention and/or treatment of a hyper-proliferative disorder of a subject.

Alternatively, the use of a non-digestible oligosaccharide according to a first aspect of the present invention may be directed the preparation of a food or drink product for the prevention and/or treatment of a proliferative disorder of a subject. More specifically, the use of a non-digestible oligosaccharide according to a first aspect of the present invention may be directed to the preparation of a food or drink product for the prevention and/or treatment of a hyper-proliferative disorder of a subject.

The use of a non-digestible oligosaccharide according to the first aspect of the present invention may be used in cases where the disorder is a skin disorder. Most specifically, the use of a non-digestible oligosaccharide according to the first aspect of the present invention is utilised where the skin disorder is psoriasis.

Also in accordance with the first aspect of the present invention the saccharide units [A] and [B] are each selected from the groups comprising: oligofructose, lactulose, and rhaffinose.

It is also preferred that the saccharide units [A] and [B] are joined by a β linkage, preferably a β 1-6 linkage.

Furthermore it is most preferred that the non-digestible oligosaccharide used in accordance with the first aspect of the present invention comprises oligofructose. In addition, it is preferred that in accordance with the first aspect of the present invention n in the non-digestible oligosaccharide comprises 2 to 6. More preferably n in the non-digestible oligosaccharide comprises 2 to 4.

The non-digestible oligosaccharide according to the first aspect of the present invention may be in the form of a salt thereof.

Alternatively, the non-digestible oligosaccharide according to the first aspect of the present invention may be in the form of a derivative thereof. Preferably an anhydride derivative selected from the group comprising difructose anhydride III and difructose anhydride IV.

In one preferred use according to the first aspect of the present invention the non-digestible oligosaccharide may be formulated as a pharmaceutical composition. Alternatively, in a further preferred use according to the first aspect of the present invention non-digestible oligosaccharide is formulated as a nutritional product.

Therefore, according to a second aspect of the present invention there is provided a pharmaceutical composition or nutritional product prepared using a non-digestible oligosaccharide as described in relation to the first aspect of the present invention.

According to another aspect of the present invention, there is provided a non-digestible oligosaccharide for use in the prevention and/or treatment of a proliferative, particularly a hyper-proliferative, skin disorder of a subject. There is also provided the use of a non-digestible oligosaccharide in the manufacture of a medicament for use in the prevention and/or treatment of a proliferative, particularly a hyper-proliferative, skin disorder of a subject.

According to another aspect of the present invention, there is provided a method for the prevention and/or treatment of a proliferative, particularly a hyper-proliferative, skin disorder of a subject in need thereof, which method comprises administering to said subject a therapeutically effective amount of a non-digestible oligosaccharide.

According to another aspect of the present invention, there is provided a non-digestible oligosaccharide for use in the prevention and/or treatment of psoriasis (especially plaque psoriasis) of a subject. There is also provided the use of a non-digestible oligosaccharide in the manufacture of a medicament for use in the prevention and/or treatment of psoriasis (especially plaque psoriasis) of a subject.

According to another aspect of the present invention, there is provided a method for the prevention and/or treatment of psoriasis (especially plaque psoriasis) of a subject in need thereof, which method comprises administering to said subject a therapeutically effective amount of a non-digestible oligosaccharide.

As discussed above, the present inventors have appreciated that non-digestible oligosaccharides may access and influence organs other than the gut and in particular may directly modify cellular functions in the skin, particularly in the epidermis, especially in keratinocytes. Such properties of the non-digestible oligosaccharides have not previously been disclosed or suggested. Thus, the present invention is believed to address the problem of hyper-proliferation in subjects, especially in subjects suffering from hyper-proliferative skin disorders. There has previously been no disclosure or suggestion of the use of non-digestible oligosaccharides in the prevention and/or treatment of such skin disorders, for example of psoriasis.

Non-digestible oligosaccharides exhibit low or no toxicity to a subject (such as animals, especially warm-blooded animals such as man) and are well tolerated at conventional doses. This means that the non-digestible oligosaccharides are advantageous in use in the prevention and/or treatment of skin disorders such as psoriasis, being easily accessible to patients and potentially improving patient compliance and usage in wide patient populations and for longer treatment regimes, for example compared to alternative medicaments currently in use. Non-digestible oligosaccharides also are expected to be useful in treating the entire body surface of subjects when required.

The non-digestible oligosaccharide may be used as described herein in any suitable form, for example as discussed herein. For example the non-digestible oligosaccharide may be used in a form for oral or topical administration.

References to the manufacture of medicaments relate to medicaments in any suitable form, including for example medicaments in the form of pharmaceutical compositions as described herein.

A non-digestible oligosaccharide as described herein may be used as a sole therapy or in combination with a conventional therapy for the prevention and/or treatment of a disorder as described herein, for example for the prevention and/or treatment of a proliferative, particularly hyper-proliferative, disorder, such as a hyper-proliferative skin disorder (particularly psoriasis). Suitable such conventional therapies would be well known to persons skilled in the art. For example, conventional therapies for the prevention and/or treatment of hyper-proliferative skin disorders such as psoriasis include treatment with coal tar, corticosteroids, calcipotriene, retinoids (such as anthralin) and/or biologicals and immune suppression drugs (such as methotrexate) and/or treatment with phototherapy. For example, a non-digestible oligosaccharide may be used in combination with phototherapy, and optionally a further conventional therapy, for the prevention and/or treatment of hyper-proliferative skin disorders such as psoriasis (especially plaque psoriasis). One or more conventional therapies may be used in combination with the non-digestible oligosaccharides as discussed herein.

According to another aspect of the present invention, there is provided a non-digestible oligosaccharide for use in producing an anti-proliferative effect in a subject, wherein the non-digestible oligosaccharide is for use in combination with a conventional therapy (for example a conventional therapy for producing an anti-proliferative effect). There is also provided the use of a non-digestible oligosaccharide in the manufacture of a medicament for use in producing an anti-proliferative effect of a subject, wherein the medicament is for use in combination with a conventional therapy (for example a conventional therapy for producing an anti-proliferative effect).

There is also provided a method for producing an anti-proliferative effect in a subject in need thereof, which method comprises administering to said subject a therapeutically effective amount of a non-digestible oligosaccharide prior to and/or during and/or after (particularly prior to and/or during) a conventional therapy (for example a conventional therapy for producing an anti-proliferative effect).

According to another aspect of the present invention, there is provided a non-digestible oligosaccharide for use in inhibiting hyper-proliferation in a subject, wherein the non-digestible oligosaccharide is for use in combination with a conventional therapy (for example a conventional therapy for inhibiting hyper-proliferation in a subject). There is also provided the use of a non-digestible oligosaccharide in the manufacture of a medicament for use in inhibiting hyper-proliferation in a subject, wherein the medicament is for use in combination with a conventional therapy (for example a conventional therapy for inhibiting hyper-proliferation in a subject).

There is also provided a method for inhibiting hyper-proliferation in a subject in need thereof, which method comprises administering to said subject a therapeutically effective amount of a non-digestible oligosaccharide prior to and/or during and/or after (particularly prior to and/or during) a conventional therapy (for example a conventional therapy for inhibiting hyper-proliferation in a subject).

According to another aspect of the present invention, there is provided a non-digestible oligosaccharide for use in inhibiting epidermal hyper-proliferation in a subject, wherein the non-digestible oligosaccharide is for use in combination with a conventional therapy (for example a conventional therapy for inhibiting epidermal hyper-proliferation in a subject). There is also provided the use of a non-digestible oligosaccharide in the manufacture of a medicament for use in inhibiting epidermal hyper-proliferation in a subject, wherein the medicament is for use in combination with a conventional therapy (for example a conventional therapy for inhibiting epidermal hyper-proliferation in a subject).

There is also provided a method for inhibiting epidermal hyper-proliferation in a subject in need thereof, which method comprises administering to said subject a therapeutically effective amount of a non-digestible oligosaccharide prior to and/or during and/or after (particularly prior to and/or during) a conventional therapy (for example a conventional therapy for inhibiting epidermal hyper-proliferation in a subject).

According to another aspect of the present invention, there is provided a non-digestible oligosaccharide for use in inhibiting keratinocyte hyper-proliferation in a subject, wherein the non-digestible oligosaccharide is for use in combination with a conventional therapy (for example a conventional therapy for inhibiting keratinocyte hyper-proliferation in a subject). There is also provided the use of a non-digestible oligosaccharide in the manufacture of a medicament for use in inhibiting keratinocyte hyper-proliferation in a subject, wherein the medicament is for use in combination with a conventional therapy (for example a conventional therapy for inhibiting keratinocyte hyper-proliferation in a subject).

There is also provided a method for inhibiting keratinocyte hyper-proliferation in a subject in need thereof, which method comprises administering to said subject a therapeutically effective amount of a non-digestible oligosaccharide prior to and/or during and/or after (particularly prior to and/or during) a conventional therapy (for example a conventional therapy for inhibiting keratinocyte hyper-proliferation in a subject).

According to another aspect of the invention, there is provided a non-digestible oligosaccharide for use in combination with a conventional therapy for the prevention and/or treatment of a proliferative disorder of a subject. According to another aspect of the invention, there is provided the use of a non-digestible oligosaccharide in the manufacture of a medicament for use in combination with a conventional therapy for the prevention and/or treatment of a proliferative disorder of a subject.

There is also provided a method for the prevention and/or treatment of a proliferative disorder of a subject in need thereof, which method comprises administering to said subject a therapeutically effective amount of a non-digestible oligosaccharide prior to and/or during and/or after (particularly prior to and/or during) a conventional therapy for the prevention and/or treatment of a proliferative disorder of a subject.

According to another aspect of the invention, there is provided a non-digestible oligosaccharide for use in the prevention and/or treatment of a proliferative disorder of a subject, wherein the non-digestible oligosaccharide is for use in combination with a conventional therapy for the prevention and/or treatment of a proliferative disorder of a subject. According to another aspect of the invention, there is provided the use of a non-digestible oligosaccharide in the manufacture of a medicament for use in the prevention and/or treatment of a proliferative disorder of a subject, wherein the medicament is for use in combination with a conventional therapy for the prevention and/or treatment of a proliferative disorder of a subject.

There is also provided a method for the prevention and/or treatment of a proliferative disorder of a subject in need thereof, which method comprises administering to said subject a therapeutically effective amount of a non-digestible oligosaccharide for use in the prevention and/or treatment of a proliferative disorder in said subject prior to and/or during and/or after (particularly prior to and/or during) a conventional therapy for the prevention and/or treatment of a proliferative disorder of a subject.

According to another aspect of the invention, there is provided a non-digestible oligosaccharide for use in combination with a conventional therapy for the prevention and/or treatment of a hyper-proliferative disorder of a subject. According to another aspect of the invention, there is provided the use of a non-digestible oligosaccharide in the manufacture of a medicament for use in combination with a conventional therapy for the prevention and/or treatment of a hyper-proliferative disorder of a subject.

There is also provided a method for the prevention and/or treatment of a hyper-proliferative disorder of a subject in need thereof, which method comprises administering to said subject a therapeutically effective amount of a non-digestible oligosaccharide prior to and/or during and/or after (particularly prior to and/or during) a conventional therapy for the prevention and/or treatment of a hyper-proliferative disorder of a subject.

According to another aspect of the invention, there is provided a non-digestible oligosaccharide for use in the prevention and/or treatment of a hyper-proliferative disorder of a subject, wherein the non-digestible oligosaccharide is for use in combination with a conventional therapy for the prevention and/or treatment of a hyper-proliferative disorder of a subject. According to another aspect of the invention, there is provided the use of a non-digestible oligosaccharide in the manufacture of a medicament for use in the prevention and/or treatment of a hyper-proliferative disorder of a subject, wherein the medicament is for use in combination with a conventional therapy for the prevention and/or treatment of a hyper-proliferative disorder of a subject.

There is also provided a method for the prevention and/or treatment of a hyper-proliferative disorder of a subject in need thereof, which method comprises administering to said subject a therapeutically effective amount of a non-digestible oligosaccharide for use in the prevention and/or treatment of a hyper-proliferative disorder in said subject prior to and/or during and/or after (particularly prior to and/or during) a conventional therapy for the prevention and/or treatment of a hyper-proliferative disorder of a subject.

According to another aspect of the invention, there is provided a non-digestible oligosaccharide for use in combination with a conventional therapy for the prevention and/or treatment of a proliferative, particularly a hyper-proliferative, skin disorder of a subject. According to another aspect of the invention, there is provided the use of a non-digestible oligosaccharide in the manufacture of a medicament for use in combination with a conventional therapy for the prevention and/or treatment of a proliferative, particularly a hyper-proliferative, skin disorder of a subject.

There is also provided a method for the prevention and/or treatment of a proliferative, particularly a hyper-proliferative, skin disorder of a subject in need thereof, which method comprises administering to said subject a therapeutically effective amount of a non-digestible oligosaccharide prior to and/or during and/or after (particularly prior to and/or during) a conventional therapy for the prevention and/or treatment of a proliferative, particularly a hyper-proliferative, skin disorder of a subject.

According to another aspect of the invention, there is provided a non-digestible oligosaccharide for use in the prevention and/or treatment of a proliferative, particularly a hyper-proliferative, skin disorder of a subject, wherein the non-digestible oligosaccharide is for use in combination with a conventional therapy for the prevention and/or treatment of a proliferative, particularly a hyper-proliferative, skin disorder of a subject. According to another aspect of the invention, there is provided the use of a non-digestible oligosaccharide in the manufacture of a medicament for use in the prevention and/or treatment of a proliferative, particularly a hyper-proliferative, skin disorder of a subject, wherein the medicament is for use in combination with a conventional therapy for the prevention and/or treatment of a proliferative, particularly a hyper-proliferative, skin disorder of a subject.

There is also provided a method for the prevention and/or treatment of a proliferative, particularly a hyper-proliferative, skin disorder of a subject in need thereof, which method comprises administering to said subject a therapeutically effective amount of a non-digestible oligosaccharide for use in the prevention and/or treatment of a proliferative, particularly a hyper-proliferative, skin disorder in said subject prior to and/or during and/or after (particularly prior to and/or during) a conventional therapy for the prevention and/or treatment of a proliferative, particularly a hyper-proliferative, skin disorder of a subject.

According to another aspect of the invention, there is provided a non-digestible oligosaccharide for use in combination with a conventional therapy for the prevention and/or treatment of psoriasis (especially plaque psoriasis) in a subject. According to another aspect of the invention, there is provided the use of a non-digestible oligosaccharide in the manufacture of a medicament for use in combination with a conventional therapy for the prevention and/or treatment of psoriasis (especially plaque psoriasis) in a subject.

There is also provided a method for the prevention and/or treatment of a psoriasis (especially plaque psoriasis) in a subject in need thereof, which method comprises administering to said subject a therapeutically effective amount of a non-digestible oligosaccharide prior to and/or during and/or after (particularly prior to and/or during) a conventional therapy for the prevention and/or treatment of psoriasis (especially plaque psoriasis) in a subject.

According to another aspect of the invention, there is provided a non-digestible oligosaccharide for use in the prevention and/or treatment of psoriasis (especially plaque psoriasis) in a subject, wherein the non-digestible oligosaccharide is for use in combination with a conventional therapy for the prevention and/or treatment of psoriasis (especially plaque psoriasis) in a subject. According to another aspect of the invention, there is provided the use of a non-digestible oligosaccharide in the manufacture of a medicament for use in the prevention and/or treatment of psoriasis (especially plaque psoriasis) in a subject, wherein the medicament is for use in combination with a conventional therapy for the prevention and/or treatment of psoriasis (especially plaque psoriasis) in a subject.

There is also provided a method for the prevention and/or treatment of psoriasis (especially plaque psoriasis) in a subject in need thereof, which method comprises administering to said subject a therapeutically effective amount of a non-digestible oligosaccharide for use in the prevention and/or treatment of psoriasis (especially plaque psoriasis) in said subject prior to and/or during and/or after (particularly prior to and/or during) a conventional therapy for the prevention and/or treatment of psoriasis (especially plaque psoriasis) in a subject.

There may also be provided a non-digestible oligosaccharide for use in producing an anti-proliferative effect, especially for inhibiting hyper-proliferation, in a subject and/or for preventing and/or treating skin disorders as discussed herein such as psoriasis, wherein the non-digestible oligosaccharide is for use in combination with phototherapy.

According to another aspect of the present invention, there is provided a non-digestible oligosaccharide for use in producing an anti-proliferative effect in a subject, wherein the non-digestible oligosaccharide is for use in combination with phototherapy. There is also provided the use of a non-digestible oligosaccharide in the manufacture of a medicament for use in producing an anti-proliferative effect of a subject, wherein the medicament is for use in combination with phototherapy.

There is also provided a method for producing an anti-proliferative effect in a subject in need thereof, which method comprises administering to said subject a therapeutically effective amount of a non-digestible oligosaccharide prior to and/or during and/or after (particularly prior to and/or during) phototherapy treatment.

According to another aspect of the present invention, there is provided a non-digestible oligosaccharide for use in inhibiting hyper-proliferation in a subject, wherein the non-digestible oligosaccharide is for use in combination with phototherapy. There is also provided the use of a non-digestible oligosaccharide in the manufacture of a medicament for use in inhibiting hyper-proliferation in a subject, wherein the medicament is for use in combination with phototherapy.

There is also provided a method for inhibiting hyper-proliferation in a subject in need thereof, which method comprises administering to said subject a therapeutically effective amount of a non-digestible oligosaccharide prior to and/or during and/or after (particularly prior to and/or during) phototherapy treatment.

According to another aspect of the present invention, there is provided a non-digestible oligosaccharide for use in inhibiting epidermal hyper-proliferation in a subject, wherein the non-digestible oligosaccharide is for use in combination with phototherapy. There is also provided the use of a non-digestible oligosaccharide in the manufacture of a medicament for use in inhibiting epidermal hyper-proliferation in a subject, wherein the medicament is for use in combination with phototherapy.

There is also provided a method for inhibiting epidermal hyper-proliferation in a subject in need thereof, which method comprises administering to said subject a therapeutically effective amount of a non-digestible oligosaccharide prior to and/or during and/or after (particularly prior to and/or during) phototherapy treatment.

According to another aspect of the present invention, there is provided a non-digestible oligosaccharide for use in inhibiting keratinocyte hyper-proliferation in a subject, wherein the non-digestible oligosaccharide is for use in combination with phototherapy. There is also provided the use of a non-digestible oligosaccharide in the manufacture of a medicament for use in inhibiting keratinocyte hyper-proliferation in a subject, wherein the medicament is for use in combination with phototherapy.

There is also provided a method for inhibiting keratinocyte hyper-proliferation in a subject in need thereof, which method comprises administering to said subject a therapeutically effective amount of a non-digestible oligosaccharide prior to and/or during and/or after (particularly prior to and/or during) phototherapy treatment.

According to another aspect of the invention, there is provided a non-digestible oligosaccharide for use in combination with phototherapy. According to another aspect of the invention, there is provided the use of a non-digestible oligosaccharide in the manufacture of a medicament for use in combination with phototherapy.

According to another aspect of the invention, there is provided a non-digestible oligosaccharide for use in the prevention and/or treatment of a proliferative disorder of a subject, wherein the non-digestible oligosaccharide is for use in combination with phototherapy. According to another aspect of the invention, there is provided the use of a non-digestible oligosaccharide in the manufacture of a medicament for use in the prevention and/or treatment of a proliferative disorder of a subject, wherein the medicament is for use in combination with phototherapy.

There is also provided a method for the prevention and/or treatment of a proliferative disorder of a subject in need thereof, which method comprises administering to said subject a therapeutically effective amount of a non-digestible oligosaccharide prior to and/or during and/or after (particularly prior to and/or during) phototherapy.

There is also provided a method for the prevention and/or treatment of a proliferative disorder of a subject in need thereof, which method comprises administering to said subject a therapeutically effective amount of a non-digestible oligosaccharide for use in the prevention and/or treatment of a proliferative disorder in said subject prior to and/or during and/or after (particularly prior to and/or during) phototherapy.

According to another aspect of the invention, there is provided a non-digestible oligosaccharide for use in the prevention and/or treatment of a hyper-proliferative disorder of a subject, wherein the non-digestible oligosaccharide is for use in combination with phototherapy. According to another aspect of the invention, there is provided the use of a non-digestible oligosaccharide in the manufacture of a medicament for use in the prevention and/or treatment of a hyper-proliferative disorder of a subject, wherein the medicament is for use in combination with phototherapy.

There is also provided a method for the prevention and/or treatment of a hyper-proliferative disorder of a subject in need thereof, which method comprises administering to said subject a therapeutically effective amount of a non-digestible oligosaccharide prior to and/or during and/or after (particularly prior to and/or during) phototherapy.

There is also provided a method for the prevention and/or treatment of a hyper-proliferative disorder of a subject in need thereof, which method comprises administering to said subject a therapeutically effective amount of a non-digestible oligosaccharide for use in the prevention and/or treatment of a hyper-proliferative disorder in said subject prior to and/or during and/or after (particularly prior to and/or during) phototherapy.

According to another aspect of the invention, there is provided a non-digestible oligosaccharide for use in the prevention and/or treatment of a proliferative, particularly a hyper-proliferative, skin disorder of a subject, wherein the non-digestible oligosaccharide is for use in combination with phototherapy. According to another aspect of the invention, there is provided the use of a non-digestible oligosaccharide in the manufacture of a medicament for use in the prevention and/or treatment of a proliferative, particularly a hyper-proliferative, skin disorder of a subject, wherein the medicament is for use in combination with phototherapy.

There is also provided a method for the prevention and/or treatment of a proliferative, particularly a hyper-proliferative, skin disorder of a subject in need thereof, which method comprises administering to said subject a therapeutically effective amount of a non-digestible oligosaccharide prior to and/or during and/or after (particularly prior to and/or during) phototherapy.

There is also provided a method for the prevention and/or treatment of a proliferative, particularly a hyper-proliferative, skin disorder of a subject in need thereof, which method comprises administering to said subject a therapeutically effective amount of a non-digestible oligosaccharide for use in the prevention and/or treatment of a proliferative, particularly a hyper-proliferative, skin disorder in said subject prior to and/or during and/or after (particularly prior to and/or during) phototherapy.

According to another aspect of the invention, there is provided a non-digestible oligosaccharide for use in the prevention and/or treatment of psoriasis (especially plaque psoriasis) in a subject, wherein the non-digestible oligosaccharide is for use in combination with phototherapy. According to another aspect of the invention, there is provided the use of a non-digestible oligosaccharide in the manufacture of a medicament for use in the prevention and/or treatment of psoriasis (especially plaque psoriasis) in a subject, wherein the medicament is for use in combination with phototherapy.

There is also provided a method for the prevention and/or treatment of a psoriasis (especially plaque psoriasis) in a subject in need thereof, which method comprises administering to said subject a therapeutically effective amount of a non-digestible oligosaccharide prior to and/or during and/or after (particularly prior to and/or during) phototherapy.

There is also provided a method for the prevention and/or treatment of psoriasis (especially plaque psoriasis) in a subject in need thereof, which method comprises administering to said subject a therapeutically effective amount of a non-digestible oligosaccharide for use in the prevention and/or treatment of psoriasis (especially plaque psoriasis) in said subject prior to and/or during and/or after (particularly prior to and/or during) phototherapy.

Any suitable phototherapy may be used in these aspects of the invention. For example, the phototherapy may involve the exposure of the subject to ultraviolet radiation, especially narrow-band ultraviolet-B radiation (for example known as Philips TL-01 phototherapy). References herein to phototherapy include photochemotherapy (for example Psoralen plus UVA photochemotherapy, known as PUVA). Localised or whole-body phototherapy may be used. The subject may be treated with the phototherapy prior to, during and/or after the treatment with a non-digestible oligosaccharide.

The non-digestible oligosaccharide may be used in combination with a conventional therapy, such as phototherapy (including photochemotherapy), in any suitable form, for example as discussed herein. For example the non-digestible oligosaccharide may be used in a form for oral or topical administration. An oral dosage form may be used (for example a pharmaceutical composition or nutritional product for oral administration), which oral dosage form may be administered to the subject at a suitable time prior to, during and/or after (particularly prior to) the phototherapy. A topical dosage form may be used (for example a pharmaceutical composition for topical administration), which may be applied to the skin of the subject at a suitable time prior to, during and/or after (particularly prior to) the phototherapy.

The inventors have appreciated that by administering the non-digestible oligosaccharide in combination with a conventional therapy, such as phototherapy, prevention and/or treatment may be further improved. In other words, the pharmaceutical compositions, nutritional products and uses of the present invention are believed to improve response to phototherapy. This is turn may advantageously decrease phototherapy times, improve patient compliance and reduce treatment costs.

The non-digestible oligosaccharide may be provided for the uses discussed above in any suitable form, including for example in a form for administration alone and/or formulated as a pharmaceutical composition, cosmetic composition or nutritional product (or nutraceutical).

There is further provided a non-digestible oligosaccharide for use as described herein, wherein the non-digestible oligosaccharide is formulated as a pharmaceutical composition. There is further provided a non-digestible oligosaccharide for use as described herein, wherein the non-digestible oligosaccharide is formulated as a nutritional product (or nutraceutical).

There is further provided a pharmaceutical composition comprising a non-digestible oligosaccharide (for example a pharmaceutical composition as described herein) for any use as described herein. There is further provided a nutritional product comprising a non-digestible oligosaccharide (for example a nutritional product (or nutraceutical) as described herein) for any use as described herein.

According to another aspect of the present invention, there is provided a pharmaceutical composition comprising a therapeutically effective amount of a non-digestible oligosaccharide (as the active ingredient) in combination with a pharmaceutically-acceptable diluent or carrier.

By a pharmaceutical composition we mean a composition including an active ingredient that is suitable for administration to a subject so as to treat and/or prevent a medical disorder/disease. An active ingredient is an agent that is effective against a disorder/disease, such that when it is administered to a subject suffering from the disorder/disease it causes reduction, remission, or regression of the disorder/disease. In order words, the active ingredient is effective to treat a disorder/disease by causing reduction, remission, or regression of the disorder/disease. An active ingredient is also typically effective in the prevention of a disorder/disease upon administration to a subject, that is, so as to prevent and/or delay onset of the disorder/disease.

The pharmaceutical composition of the invention comprises the non-digestible oligosaccharide as the active ingredient (that is such that when the non-digestible oligosaccharide thereof is administered to a subject suffering from a disorder, for example as described herein, it causes prevention, reduction, remission and/or regression of the disorder).

Any suitable pharmaceutically-acceptable diluent or carrier may be included in the pharmaceutical compositions of the invention, which diluents or carriers would be well known to persons skilled in the art. The particular diluents or carriers selected depend on various factors, including the dosage of the non-digestible oligosaccharide, the mode of administration of the composition and the stability of the non-digestible oligosaccharide. The pharmaceutically-acceptable diluent or carrier should be selected so as to deliver a sufficient amount of the non-digestible oligosaccharide to the skin.

Suitable pharmaceutical carriers for use in accordance with the present invention may include but are not limited to: inert solid diluents or fillers, sterile aqueous solutions and various organic solvents. Examples of solid carriers comprise lactose, terra alba, sucrose, cyclodextrin, talc, gelatine, agar, pectin, acacia, magnesium stearate, stearic acid or lower alkyl ethers of cellulose.

Examples of liquid carriers comprise syrup, peanut oil, olive oil, phospholipids, fatty acids, fatty acid amines, polyoxyethylene, isopropyl myristate or water. Similarly, the carrier or diluent may include any sustained release material known in the art, such as for example glycerol monostearate or glycerol distearate, alone or mixed with wax.

The pharmaceutical compositions of the invention may be formulated for administration by any convenient route. For example, the pharmaceutical compositions may be in a form suitable for oral administration (for example as tablets, lozenges, hard or soft capsules, aqueous or oily suspensions, emulsions, dispersible powders or granules, syrups or elixirs), for topical administration (for example as creams, ointments, gels, or aqueous or oily solutions or suspensions, or by transdermal delivery), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

According to another aspect of the invention, there is provided a pharmaceutical composition comprising a therapeutically effective amount of a non-digestible oligosaccharide (as the active ingredient) in combination with a pharmaceutically-acceptable diluent or carrier, wherein the pharmaceutical composition is formulated for oral administration.

It will be appreciated that the preferred route of administration will depend on the general condition and age of the subject to be treated, the nature of the disorder to be treated and the non-digestible oligosaccharide chosen.

Pharmaceutical compositions for oral administration may be for example in a solid dosage form such as capsules, tablets, dragees, pills, lozenges, powders and granules. Solid dosage forms may further comprise one or more substances which may also act as flavoring agents, lubricants, solubilizers, suspending agents, fillers, glidants, compression aids, binders or tablet-disintegrating agents. In powders, the vehicle is often a finely divided solid which is in admixture with the active ingredient. In tablets, the active ingredient may be mixed with a vehicle having the necessary compression properties in suitable proportions and compacted in the shape and size desired. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Where appropriate, solid dosage forms can be prepared with coatings such as enteric coatings or they can be formulated so as to provide controlled release of the non-digestible oligosaccharide such as sustained or prolonged release or bolus application according to the methods well known in the art.

Pharmaceutical compositions for oral administration may alternatively be in a liquid form. A liquid carrier may be in the form of for example solutions, suspensions, emulsions, syrups, elixirs and pressurized compositions. The active ingredient can be dissolved or suspended in a pharmaceutically-acceptable liquid vehicle such as water (optionally flavoured), an organic solvent, a mixture of both or pharmaceutically-acceptable oils or fats. The liquid vehicle may further comprise other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid vehicles for oral administration include for example water (partially containing additives as above, for example cellulose derivatives, preferably sodium carboxymethyl cellulose solution), alcohols (including monohydric alcohols and polyhydric alcohols, for example glycols) and their derivatives, and oils (for example fractionated coconut oil and arachis oil).

The pharmaceutical compositions of the invention may be presented in the form of unit dosage forms containing a defined amount of the non-digestible oligosaccharide. Such unit dosage forms are preferably selected so as to achieve a desired level of biological activity.

In one aspect, the pharmaceutical composition of the present invention may be preferably formulated for oral administration, for example as a discrete unit in the form of a tablet or capsule each containing a predetermined amount of the non-digestible oligosaccharide and a suitable pharmaceutically-acceptable carrier or diluent.

Alternatively, the non-digestible oligosaccharide may be formulated as a powder, granule or semisolid for incorporation into capsules. For presentation in the form of a semisolid, the non-digestible oligosaccharide may be dissolved or suspended in a viscous liquid or semisolid vehicle such as a polyethylene glycol, or a liquid carrier such as for example a glycol (for example propylene glycol or glycerol) or a vegetable or fish oil (for example an oil selected from olive oil, sunflower oil, safflower oil, evening primrose oil, soya oil, cod liver oil, herring oil, etc). This composition may then be filled into capsules of either the hard gelatine or soft gelatine type or made from hard or soft gelatine equivalents, soft gelatine or gelatine-equivalent capsules being preferred for viscous liquid or semisolid fillings.

The non-digestible oligosaccharide may also be formulated as a powder for dissolving or suspending in a suitable liquid carrier.

Powder forms of the non-digestible oligosaccharide may be prepared by any suitable method, including for example freeze-drying or spray drying, and typically are available from commercially sources, for example synthesised according to desired Good Manufacturing Practice (GMP).

Powder forms of the non-digestible oligosaccharide may be incorporated into slow-release capsules or devices which may be ingested and are able to release the non-digestible oligosaccharide into the intestines over a long period of time.

The non-digestible oligosaccharide may also be microencapsulated. For instance encapsulation may be by calcium-alginate gel capsule formation.

Kappa-carrageenan, gellan gum, gelatin and starch may be used as excipients for micro-encapsulation.

In another aspect, the pharmaceutical composition of the present invention may be formulated for topical administration, including for administration directly to the skin of a subject, for example at an area requiring treatment.

Pharmaceutical compositions for topical administration may for example be in the form of solutions, creams, ointments, jellies, gels, sprays, foams, powders, liposomes, or aqueous or oily solutions or suspensions. Suitable diluents and carriers include, for example, peanut oil, water, ethyl cocoate, octyl cocoate, polyoxyethylenated hydrogenated caster oil, liquid paraffin, isopropanol, glycerol, propylene glycol, paraffin, celluloses, parabens, stearyl alcohol, polyethylene glycol, isopropyl myristate and phenoxyethanol.

In the case of topical application to the scalp, the pharmaceutical composition may be formulated as a shampoo. In the case of topical application to the skin, the pharmaceutical composition may be formulated as an additive to wash water (for example in the form of a bath or shower gel or cream), such as to bath water etc. Such pharmaceutical compositions for topical administration may further include diluents or carriers that are also suitable for use in cosmetics Pharmaceutical compositions for topical administration by application to the skin may further comprise moisturisers, and sun tan lotions and creams.

In the case of pharmaceutical compositions for topical administration by application to the skin, the diluent or carrier is preferably selected so as to assist the transport of the active ingredient across the skin barrier and may need to be one capable of crossing the keratinous layer of the skin. Examples of suitable diluents/carriers for this purpose include but are not limited to: dimethyl sulfoxide and acetic acid. Many methods are known for preparation of pharmaceutical compositions for topical application. For example, the non-digestible oligosaccharide may be mixed with known carrier materials as discussed herein.

Suitable pharmaceutical compositions for topical administration may further comprise a known chemical absorption promoter. Examples of absorption promoters are for example dimethylacetamide (as described in U.S. Pat. No. 3,472,931), trichloroethanol or trifluoroethanol (as described in U.S. Pat. No. 3,891,757) certain alcohols and mixtures thereof (as described in GB-1,001,949). A carrier material for topical application to unbroken skin is also described in GB-1,464,975, which discloses a carrier material consisting of a solvent comprising 40 to 70% (volume/volume) isopropanol and 0 to 60% (volume/volume) glycerol, the balance, if any, being an inert constituent of a diluent not exceeding 40% of the total volume of solvent.

Alternatively, as will be appreciated by one skilled in the art, an administration may be achieved by means of localised injection, for example intra-dermal injection.

Alternatively, the skilled person will also appreciate that topical administration may be achieved by means of diffusion from or through a suitable material to the skin, that is, wherein the non-digestible oligosaccharide is releasably contained in or applied to the material for release to the skin upon contact therewith. For example, suitable materials may be provided in the form of a garment, preferably a garment in direct contact with the skin such as for example but not limited to: gloves, socks or tights, whereby contact with the skin is achieved when the subject wears the garment. An example of a suitable such garment is disclosed, for example, in U.S. Pat. No. 5,614,202 the specific teachings of which are incorporated herein by reference.

The non-digestible oligosaccharide is present in the pharmaceutical composition in a therapeutically effective amount. A "therapeutically effective amount" is any amount of the non-digestible oligosaccharide (for example as contained in the pharmaceutical composition as described herein) which, when administered to a subject suffering from a disorder against which it is effective, causes prevention, reduction, remission and/or regression of the disorder.

The therapeutically effective amount of non-digestible oligosaccharide that is combined with the pharmaceutically-acceptable diluent or carrier to produce a single dosage form will necessarily vary depending upon the nature and severity of the disorder (such as a hyper-proliferative skin disorder) treated, the particular patient treated and the particular route of administration, according to well known principles of medicine. For example, a composition formulated for oral administration to man will generally comprise from about 0.5 mg to 7 g of active constituent. Preferably, a composition formulated for oral administration to man will comprise from 0.1 g to 7 g of a non-digestible oligosaccharide in the form of an active constituent. More preferably a composition formulated for oral administration to man will comprise from 1 g to 7 g of active constituent. Most preferably a composition formulated for oral administration to man will generally comprise from 2.5 g to 5 g of active constituent. In all cases the composition may be compounded with an appropriate and convenient amount of diluent/carrier which may vary from between 5 to 98 percent by weight of the total composition.

Typically, unit dosage forms for oral administration, such as tablets and capsules, will contain from 0.5 mg to 1 g (for example from 0.5 mg to 0.5 g) of a non-digestible oligosaccharide as the active ingredient. For example, unit dosage forms such as tablets and capsules for oral administration may preferably comprise from 0.2 g to 1 g. More preferably unit dosage forms such as tablets and capsules for oral administration may comprise 0.2 g to 0.5 g of a non-digestible oligosaccharide as the active ingredient.

Typically, unit dosage forms for oral administration, such as powders or liquid forms (for example wherein the non-digestible oligosaccharide is dissolved or suspended in a pharmaceutically-acceptable liquid vehicle), will comprise from 1 g to 40 g of a non-digestible oligosaccharide as the active ingredient.

Typically, compositions for topical administration (such as a cream) will comprise from 0.5 to 80%. More preferably, compositions for topical administration (such as a cream) will comprise from 0.5 to 50%. Most preferably however, compositions for topical administration (such as a cream) will comprise from, 1 to 25% by weight of the total composition of a non-digestible oligosaccharide as the active ingredient.

The pharmaceutical compositions of the present invention may be obtained by conventional procedures using conventional pharmaceutical diluents or carriers, well known in the art.

The pharmaceutical composition of the invention may be provided for any of the uses as described herein. The pharmaceutical composition of the invention may be provided for the prevention and/or treatment of a proliferative, especially a hyper-proliferative, skin disorder (such as psoriasis) in a subject as discussed herein.

According to the present invention, there is also provided a pharmaceutical composition for use in producing an anti-proliferative effect in a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in producing an anti-proliferative effect in a subject.

According to the present invention, there is also provided a method for producing an anti-proliferative effect in a subject in need thereof, which method comprises administering to said subject a therapeutically effective amount of a pharmaceutical composition comprising a therapeutically effective amount of a non-digestible oligosaccharide as the active ingredient.

According to the present invention, there is also provided a pharmaceutical composition for use in inhibiting hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in inhibiting hyper-proliferation in a subject.

According to the present invention, there is also provided a method for inhibiting hyper-proliferation in a subject in need thereof, which method comprises administering to said subject a therapeutically effective amount of a pharmaceutical composition comprising a therapeutically effective amount of a non-digestible oligosaccharide as the active ingredient.

According to the present invention, there is also provided a pharmaceutical composition for use in inhibiting epidermal hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in inhibiting epidermal hyper-proliferation in a subject.

According to the present invention, there is also provided a method for inhibiting epidermal hyper-proliferation in a subject in need thereof, which method comprises administering to said subject a therapeutically effective amount of a pharmaceutical composition comprising a therapeutically effective amount of a non-digestible oligosaccharide as the active ingredient.

According to the present invention, there is also provided a pharmaceutical composition for use in inhibiting keratinocyte hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in inhibiting keratinocyte hyper-proliferation in a subject.

According to the present invention, there is also provided a method for inhibiting keratinocyte hyper-proliferation in a subject in need thereof, which method comprises administering to said subject a therapeutically effective amount of a pharmaceutical composition comprising a therapeutically effective amount of a non-digestible oligosaccharide as the active ingredient.

According to the present invention, there is also provided a pharmaceutical composition for use in the prevention and/or treatment of a proliferative, particularly a hyper-proliferative, skin disorder of a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in the prevention and/or treatment of a proliferative, particularly a hyper-proliferative, skin disorder.

According to the present invention, there is also provided a method of preventing and/or treating a proliferative, particularly a hyper-proliferative, skin disorder of a subject in need thereof, which method comprises administering to said subject a therapeutically effective amount of a pharmaceutical composition comprising a therapeutically effective amount of a non-digestible oligosaccharide as the active ingredient.

According to the present invention, there is also provided a pharmaceutical composition for use in the prevention and/or treatment of psoriasis (especially plaque psoriasis) in a subject, wherein the pharmaceutical composition comprises a therapeutically effective amount of a non-digestible oligosaccharide as the active ingredient. There is also provided the use of a non-digestible oligosaccharide in the manufacture of a pharmaceutical composition for use in the prevention and/or treatment of psoriasis (especially plaque psoriasis).

According to the present invention, there is also provided a method preventing and/or treating psoriasis (especially plaque psoriasis) in a subject in need thereof, which method comprises administering to said subject a therapeutically effective amount of a pharmaceutical composition comprising a therapeutically effective amount of a non-digestible oligosaccharide as the active ingredient.

The non-digestible oligosaccharide as described herein may be formulated for administration to a subject as a nutritional product or nutraceutical. Such products may be used as staple foods as well as under circumstances where there may be a clinical need. For example, the product may be used as a pet foodstuff.

Accordingly, there is provided a nutritional product (or nutraceutical) comprising a therapeutically effective amount of a non-digestible oligosaccharide (as the active ingredient).

The nutritional product (or nutraceutical) of the invention may be provided for any of the uses as described herein. The nutritional product (or nutraceutical) of the invention may be provided for the prevention and/or treatment of a proliferative, especially hyper-proliferative, skin disorder (such as psoriasis, especially plaque psoriasis) in a subject as discussed herein According to the present invention, there is also provided a nutritional product (or nutraceutical) for use in producing an anti-proliferative effect in a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in producing an anti-proliferative effect in a subject.

According to the present invention, there is also provided a method for producing an anti-proliferative effect in a subject in need thereof, which method comprises administering to said subject a therapeutically effective amount of a nutritional product (or nutraceutical) comprising a therapeutically effective amount of a non-digestible oligosaccharide as the active ingredient.

According to the present invention, there is also provided a nutritional product (or nutraceutical) use in inhibiting hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in inhibiting hyper-proliferation in a subject.

According to the present invention, there is also provided a method for inhibiting hyper-proliferation in a subject in need thereof, which method comprises administering to said subject a therapeutically effective amount of a nutritional product (or nutraceutical) comprising a therapeutically effective amount of a non-digestible oligosaccharide as the active ingredient.

According to the present invention, there is also provided a nutritional product (or nutraceutical) for use in inhibiting epidermal hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in inhibiting epidermal hyper-proliferation in a subject.

According to the present invention, there is also provided a method for inhibiting epidermal hyper-proliferation in a subject in need thereof, which method comprises administering to said subject a therapeutically effective amount of a nutritional product (or nutraceutical) comprising a therapeutically effective amount of a non-digestible oligosaccharide as the active ingredient.

According to the present invention, there is also provided a nutritional product (or nutraceutical) for use in inhibiting keratinocyte hyper-proliferation effect in a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in inhibiting keratinocyte hyper-proliferation in a subject.

According to the present invention, there is also provided a method for inhibiting keratinocyte hyper-proliferation in a subject in need thereof, which method comprises administering to said subject a therapeutically effective amount of a nutritional product (or nutraceutical) comprising a therapeutically effective amount of a non-digestible oligosaccharide as the active ingredient.

According to the present invention, there is also provided a nutritional product (or nutraceutical) for use in the prevention and/or treatment of a proliferative, particularly a hyper-proliferative, skin disorder of a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in the prevention and/or treatment of a proliferative, particularly a hyper-proliferative, skin disorder.

According to the present invention, there is also provided a method preventing and/or treating a proliferative, particularly a hyper-proliferative, skin disorder of a subject in need thereof, which method comprises administering to said subject a therapeutically effective amount of a nutritional product (or nutraceutical) comprising a therapeutically effective amount of a non-digestible oligosaccharide as the active ingredient.

According to the present invention, there is also provided a nutritional product (or nutraceutical) for use in the prevention and/or treatment of psoriasis (especially plaque psoriasis) in a subject, wherein the pharmaceutical composition comprises a therapeutically effective amount of a non-digestible oligosaccharide as the active ingredient. There is also provided the use of a non-digestible oligosaccharide in the manufacture of a nutritional product (or nutraceutical) for use in the prevention and/or treatment of psoriasis (especially plaque psoriasis).

According to the present invention, there is also provided a method preventing and/or treating psoriasis (especially plaque psoriasis) in a subject in need thereof, which method comprises administering to said subject a therapeutically effective amount of a nutritional product (or nutraceutical) comprising a therapeutically effective amount of a non-digestible oligosaccharide as the active ingredient.

The nutritional product may take any suitable form, such as a beverage or drink, a powder or powder mix, a food bar or other solid foodstuff, and may further comprise any additional suitable ingredient(s) as well as the non-digestible oligosaccharide. Such additional ingredients may be added for nutritional or medical reasons or for improved palatability. For example, a solid form of the non-digestible oligosaccharide, such as in the form of a powder, may be incorporated into a solid foodstuff such as a food bar (for example a fruit bar, nut bar or cereal bar). For presentation in the form of a food bar, the powder can be admixed with any one or more ingredients selected from dried fruits such as for example sundried tomatoes, raisins and sultanas, ground nuts or cereals such as oats and wheat. For presentation in the form of a beverage or drink, the powder can be admixed with any one or more ingredients such as water, fruit juice and/or flavouring. A solid form of the non-digestible oligosaccharide, such as in the form of a powder, may be provided, optionally admixed with any one or more further ingredients, (for example in a suitable packaging, such as a sachet) for addition to a liquid for consumption by a subject.

Therapeutically effective amounts of a non-digestible oligosaccharide in a nutritional product may be as described above in relation to pharmaceutical compositions, particularly in relation to the pharmaceutical compositions formulated for oral administration.

A suitable nutritional product may comprise:
(a) a clear, low viscosity, water-like, stable, ready-to-use, bottled, carbonated or non-carbonated drink; or a concentrated clear liquid for reconstitution containing a non-digestible oligosaccharide;
(b) a powder/granular mix to be reconstituted with water or any other orally ingestible liquid as a drinkable liquid, containing a non-digestible oligosaccharide;
(c) a powder/granular mix mixed into a foodstuff (for example a food bar or the like).

Conventional procedures known the persons skilled in the art may be used to create the nutritional products or nutraceuticals, such as in the form of liquid drinks, powder mixes and foodstuffs, comprising the non-digestible oligosaccharide.

The amount of the active ingredient required by a subject, for example as a daily dose, is determined by biological activity and bioavailability which in turn depends on the formulation, mode of administration, the physicochemical properties of the active ingredient and whether the active ingredient is being used as a monotherapy or in a combined therapy. Generally, a daily dose for a human adult should be between 0.1 g and 40 g of the active ingredient (however formulated). More preferably a daily dose for a human adult should be between 1 g and 30 g. For example 5 g, 10 g, or 15 g as required.

The frequency of administration will also be influenced by the above-mentioned factors and particularly the half-life of the active ingredient within the subject being treated. For instance, the half-life will be influenced by the health status of the subject, gut motility and other factors.

Daily doses may be given as a single administration (for example as a daily tablet, a capsule or liquid suspension or as a nutritional product for oral consumption). Alternatively doses may be given twice or more times during a day.

The pharmaceutical composition or nutritional product of the invention may be applied as a sole therapy or may be applied in combination with a conventional therapy as discussed above. For example, the pharmaceutical composition or nutritional product of the invention may be applied in combination with phototherapy, such as narrow-band UVB phototherapy as discussed above.

The "subject" to which the active ingredient and/or pharmaceutical composition and/or nutritional product (or nutraceutical) of the invention is to be administered is an animal, by which we include mammals and birds. In particular, it is intended that the subject is a warm-blooded animal, such as a domestic animal or human, particularly a human.

A subject to be treated for a proliferative, especially a hyper-proliferative, disorder may be identified by standard diagnostic techniques for the disorder, which diagnostic techniques would be well known to persons skilled in the art.

The term a non-digestible oligosaccharide used herein is a low molecular weight carbohydrate composed of two or more saccharide units. One or more non-digestible oligosaccharides may be used in the uses, preparations and methods of the present invention as discussed herein.

Preferably, the non-digestible oligosaccharide comprises from 2 to 60 saccharide units. More preferably the non-digestible oligosaccharide comprises from 2 to 35. Most preferably the non-digestible oligosaccharide comprises from 2 to 10 saccharide units. Non-digestible oligosaccharides may comprise the saccharide units, fructose, xylose, glucose, galactose or maltose.

In particular, the non-digestible oligosaccharide may be selected from one or more of the groups comprising: oligofructose, inulin, galactooligosaccharides, glycosylsucrose, galamaltotriose, lactulose, maltooligosaccharides, stachyose and rhaffinose. Most particularly however, the non-digestible oligosaccharide is oligofructose. Oligofructose is also sometimes referred to as fructooligosaccharides or oligofructan.

For the avoidance of any doubt the structures of oligofructose, lactulose and rhaffinose are set out below:

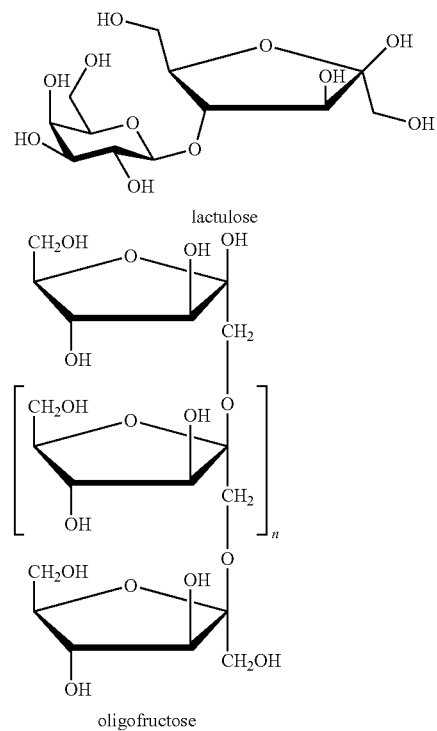

wherein n is known as the degree of polymerisation, and wherein n is typically from 2 to 10, such as for example 2 to 4.

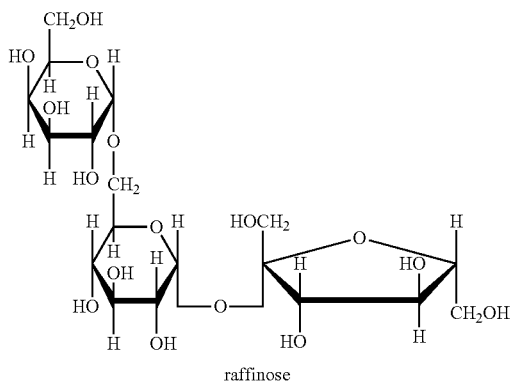

raffinose

Raffinose is a trisaccharide composed of galactose, fructose, and glucose. It can be found in beans, cabbage, brussels sprouts, broccoli, asparagus, other vegetables, and whole grains. Raffinose can be hydrolyzed to D-galactose and sucrose by the enzyme α-galactosidase (α-GAL), an enzyme not found in the human digestive tract. The enzyme does not cleave β-linked galactose, as in lactose.

The raffinose family of oligosaccharides (RFOs) are alpha-galactosyl derivatives of sucrose, and the most common are the trisaccharide raffinose, the tetrasaccharide stachyose, and the pentasaccharide verbascose. RFOs are almost ubiquitous in the plant kingdom, being found in a large variety of seeds from many different families.

Humans and other monogastric animals (pigs and poultry) do not possess the α-GAL enzyme to break down RFOs and these oligosaccharides pass undigested through the stomach and upper intestine.

Non-digestible oligosaccharides occur naturally and are readily obtainable from natural sources. Further examples of oligosaccharides include: galactooligosaccharides and mannanoligosaccharides.

Non-digestible oligosaccharides may be isolated from natural sources using well known procedures. Non-digestible oligosaccharides may for example be isolated from any suitable source, such as for example but not limited to: garlic, onion, asparagus, artichoke and chicory. Upon isolation from natural sources, the non-digestible oligosaccharides obtained may comprise additional components, such as additional sugars (for example natural sugars such as glucose, fructose and/or sucrose) and may include components of varying degrees of polymerisation. Non-digestible oligosaccharides including such additional sugars and/or having varying degrees of polymerisation may be used in the present invention, provided that they provide the desired anti-proliferative effect as discussed herein. Typically, the non-digestible oligosaccharides may include up to 40% by weight of such additional components. Examples of suitable oligofructoses include Orafti®L60, Orafti®L85, Orafti®L95, Orafti®P95 and Orafti®Synergy1.

References herein to non-digestible oligosaccharides include all possible diastereomers.

Non-digestible oligosaccharides may be provided as a solid or semi-solid, preferably as a powder.

In addition, in relation to the non-digestible oligosaccharides described herein, derivatives of the non-digestible oligosaccharides may also be used. Suitable derivatives include salts thereof, including pharmaceutically acceptable salts. In addition, difructose anhydrides may also be used which comprise two linked fructose units linked which can not be digested by most mammals including humans. Suitable difructose anhydrides include difructose anhydride III and difructose anhydride IV. Difructose anhydride III is a non-digestible disaccharide produced from inulin and is of the structure below.

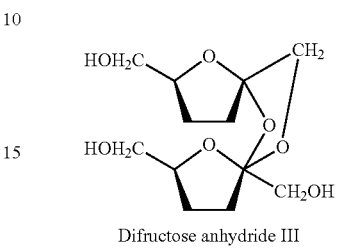

Difructose anhydride III

The invention will now be illustrated by the following non-limiting examples and drawings.

Figure 7:
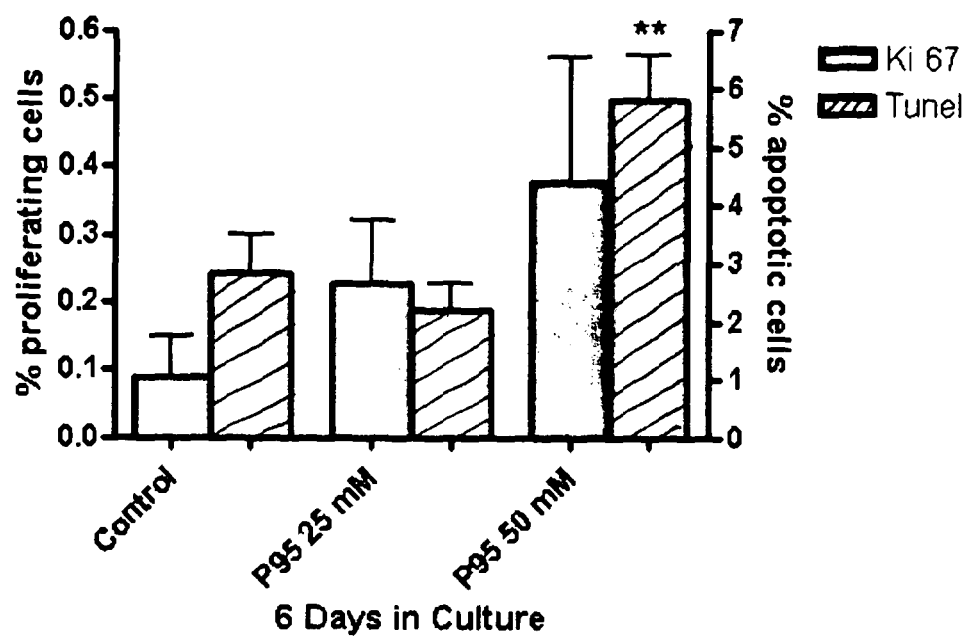

FIG. 7 illustrates a graph of Ki67/TUNEL staining in human skin maintained in organ culture. TUNEL is a measure of apoptosis. Ki67 is a measure of proliferation. It can be seen that P95 increases TUNEL staining in a dose dependent manner.

EXAMPLE 1

Cell Culture

Caco-2 cells, obtained from the European cell Culture collection (ECACC number 86010202, Porton Down, UK) were maintained in Dulbecco's modified Eagles medium (DMEM) containing high glucose (4.5 g/l), 10% Fetal calf serum, 2 Mm Glutamine, 1% non-essential amino-acids and 50 IU/ml penicillin/50 µg/ml streptomycin (Invitrogen, Paisley, UK). These cells (passages 41-50) were cultured in 75 cm$^2$ T-flasks (Fisher, UK) at 37° C. in a 5% $CO_2$, constant humidity environment with medium replaced three times a week. Monolayers were split when they reached in the region of 80% confluency at a split ratio of 1:10 using 0.05% trypsin/0.02% EDTA.

Rat epidermal keratinocytes (REK) obtained as a gift of Professor Pasonen (University of Kupoi, Finland). REK were grown routinely in Minimal Essential Medium, MEM (LifeTechnologies LTD, Paisley, Scotland) with 10% fetal bovine serum, (HyClone, Logan, Utah, USA), 4 mM L-glutamine (Sigma, St. Louis, Mo., USA) and 50 µg/ml streptomycin sulfate and 50 U/ml penicillin (Sigma) at 37° C. in humidified 95% air/5% $CO_2$. The REKs were subcultured when they reached 80% confluency and split at a ratio of 1:10 using 0.05% trypsin/0.02% EDTA.

Measurement of Transepithelial Electrical Resistance.

Transepithelial electrical resistance (TEER) involves measuring the electrical resistance across a cells monolayer. Electrical resistance is a measure of how permeable the monolayer is to ions and can therefore be used as a proxy for tight junction integrity. A high resistance indicates that the tight junctions are closed and vice versa.

Caco-2 cells were seeded on Transwell™ polycarbonate cell culture inserts with a mean pore size of 0.4 µM (Costar) at 3×105 cells/cm$^2$ and were grown for 21 days before experimental use or until the transepithelial electrical resistance (TEER) had become stable. TEER was monitored using an Evometer (World Precision Instruments, Hertfordshire, UK) fitted with Chopstick electrodes. TEER was normalised by the area of the monolayer and the background TEER of blank filters was subtracted from the TEER of the cell monolayer. Cells were placed in serum free media for 24 hours before the addition of a non-digestible oligosaccharide, oligofructose.

Treatment of Cells with Non-Digestible Oligosaccharides.

REK and Caco-2 Cells were placed in serum free medium for twenty four hours and then treated with a non-digestible oligosaccharide at varying concentrations and/or times. The non-digestible oligosaccharide were prepared as stock solutions in water at a concentration of 1 molar (M). Sucrose, a negative control, was treated similarly.

Cell Preparation for High Content Screening.

High content screening observes the activation of protein kinase C which moves within the cell when it is activated. Activation of protein kinase C is the start point of a signalling cascade within the cells which can alter numerous cellular activities. Activation of the cell regulator PKC suggests that many cellular activities are modified in response to non-digestible oligosaccharides.

Caco-2 cells were grown on 96 well plates until 100% confluent. Prior to the experiment, cells were incubated with serum free medium (SFM) and left in the incubator overnight. The next day cells were treated with either oligofructose (50 mM or 100 mM) or melibiose (50 mM or 100 mM) for 5, 10, 20, 40 or 60 minutes. All experiments were carried out in triplicate. Similarly, as a control some cells were treated with sucrose at either 50 or 100 mM for the same times as the non-digestible oligosaccharides. After this 2% formaldehyde was placed on the cells for twenty minutes at room temperature. The cells were then washed twice with PBS and left with a 100 µl PBS solution for the experiment. The cells were then challenged with a fluorescent antibody raised against protein Kinase C (PKC) and analysed by High Content Screening (HCS) using a plate reading fluorescent microscope. Plate reading-based fluorescence microscopes enable the rapid acquisition and quantification of cells stained for several antigens of interest, thereby allowing signal transduction events such as phosphorylation and/or subcellular protein redistribution to be quantified in a multiparametric fashion. High Content Screening (HCS) allows the quantification of staining intensities and subcellular localisation patterns allowing image data to be converted into a graphical format. High Content Screening (HCS) was conducted by Imagen Biotech Ltd.

Cell Proliferation Assay.

REK cells were plated in 96 well plates at 3000 cells per well. Twenty four hours later, the cells were placed in medium containing 5% foetal bovine serum (FBS) and 50 mM non-digestible oligosaccharide. The cells were grown for four days and then the cell number determined using Celltitre 96™ assay (promega) according to the manufacturers' instructions.

KI67/TUNEL Staining in Human Skin

Human skin was obtained from consenting volunteers undergoing elective surgery for face lifts. The skin was maintained in organ culture for up to seven days and treated with oligofructose. The tissue was then 'snap' frozen, sectioned and stained with appropriate antibodies for the proliferation marker, Ki67, or the marker of apoptosis, TUNEL.

Results.

Oligofructose Decreased Transepithelial Electrical Resistance in Caco-2 Cell Monolayers.

Figure 1:
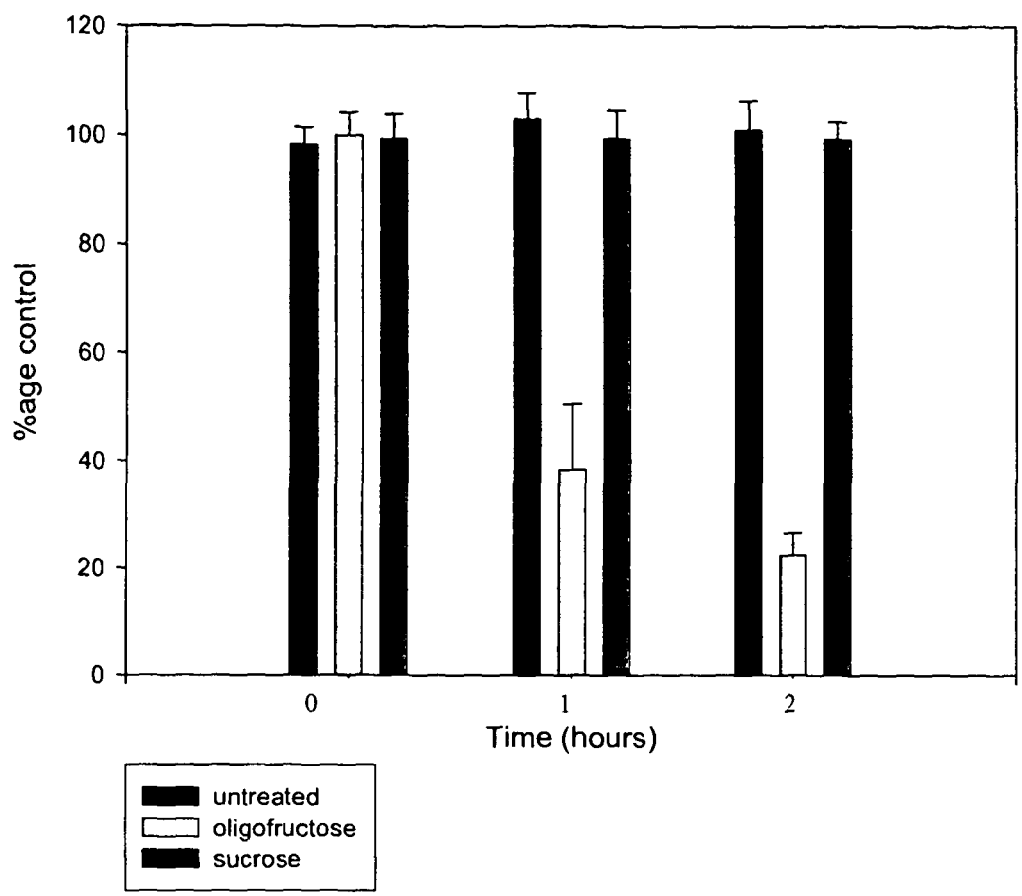
FIG. 1 shows the results of transepithelial electrical resistance (TEER) measurements in caco-2 cell monolayers for control, oligofructose and sucrose.
Figure 2:
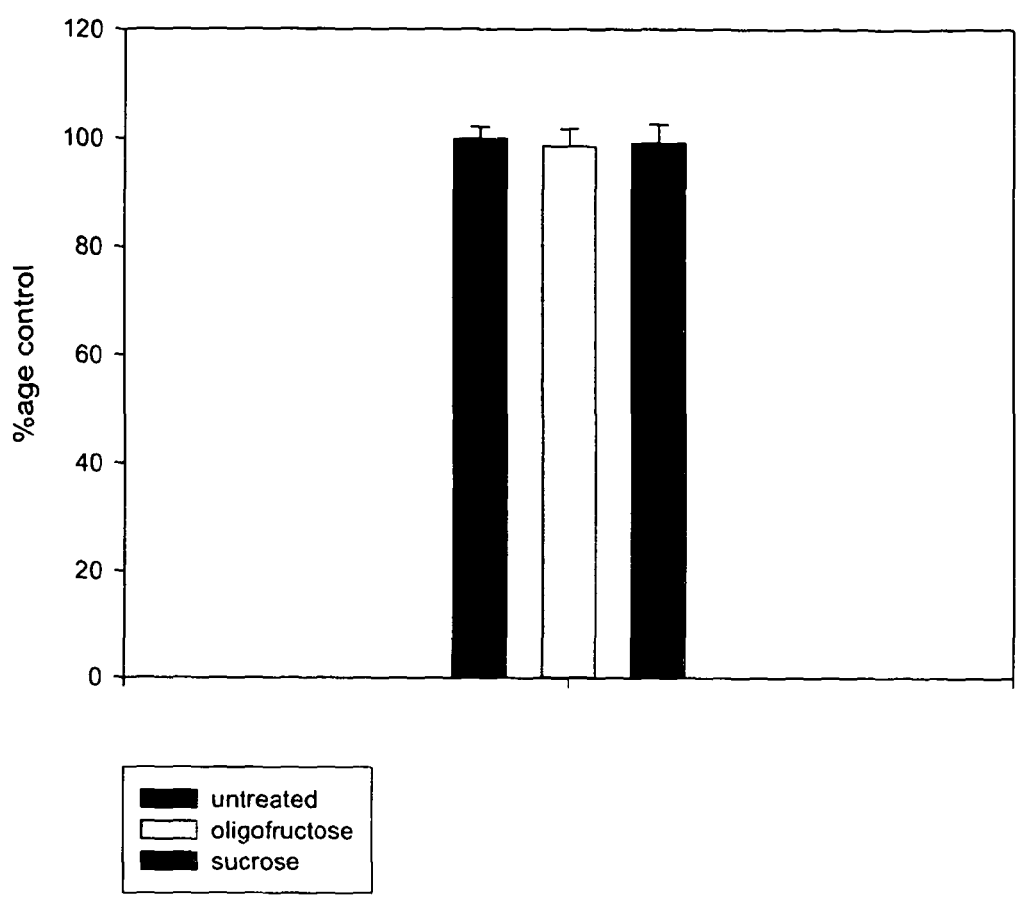
FIG. 2 shows the results of the transepithelial electrical resistance (TEER) measurements in caco-2 cell monolayers for control, oligofructose and sucrose added to the basal side.

Caco-2 monolayers growing on Tanswell™ filters were treated with 50 mM oligofructose or the same concentration of sucrose by addition of the oligofructose or sucrose to the apical surface. TEER measurements were taken for two hours along with that of an untreated control. The results are shown in FIG. 1 and demonstrate that the TEER measurements of control monolayers remained unaffected during this time period as did that of the sucrose control. However, the TEER measurements were significantly decreased by treatment with non-digestible polysaccharide. Oligofructose decreased the TEER to approximately 35% of starting values. Reductions in TEER only occurred if non-digestible polysaccharide were added to the apical surface. Basolateral treatment had no effect on the cells. The reduction in TEER shows that the cells recognise the non-digestible oligosaccharides and that the tight junctions open.

Non-Digestible Polysaccharides Induce PKC Signalling in Caco-2 Cells.

Confluent caco-2 cells growing on 96 well plates were challenged with sucrose or oligofructose for amounts of time varying between 5 and 60 minutes. Using high content screening, (a fluorescence based technique which monitors the movement of key proteins from the cytoplasm to the membrane within the cell using antibodies), movement of protein kinase C (PKC) was observed within minutes of applying oligofructose.

Figure 3:
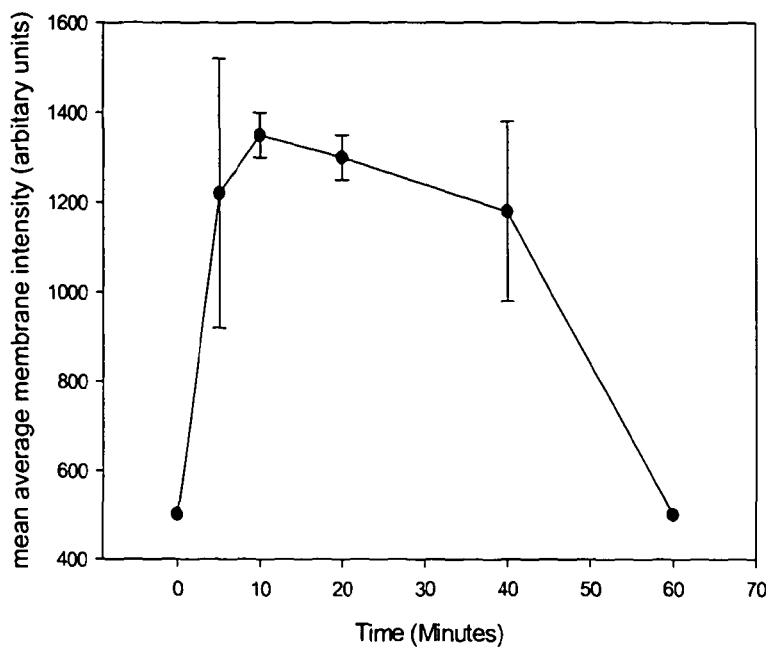
FIG. 3 shows the results of oligofructose in inducing PKC signalling in caco-2 cells.

The graph shown in FIG. 3 demonstrates the results for oligofructose and shows an increase of over four-fold above baseline in the mean membrane intensity of staining.

Figure 4:
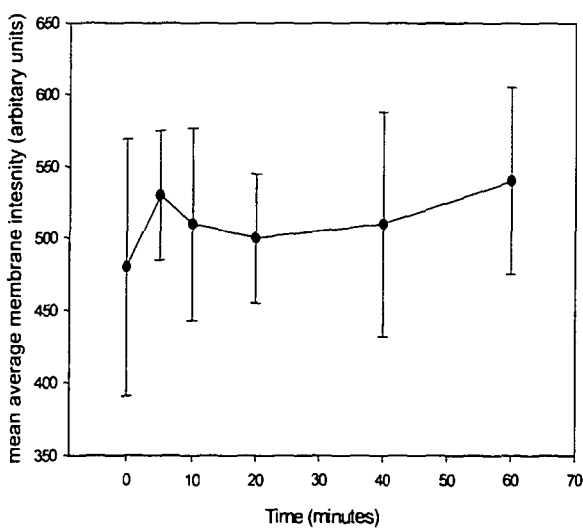
FIG. 4 shows the results of sucrose in inducing PKC signalling in caco-2 cells.

The graph shown in FIG. 4 demonstrates the results for sucrose (which is not a non-digestible oligosaccharide) and shows that sucrose did not induce any changes to PKC staining intensity at the membrane in caco-2 cells.

Non-Digestible Polysaccharides Inhibit Keratinocyte Proliferation.

Rat epidermal keratinocytes growing in 96 well plates were subjected to a reduced serum (5%) medium containing 50 mM non-digestible oligosaccharide and then incubated for four days. Cell proliferation was monitored using Celltitre96.

Figure 5:
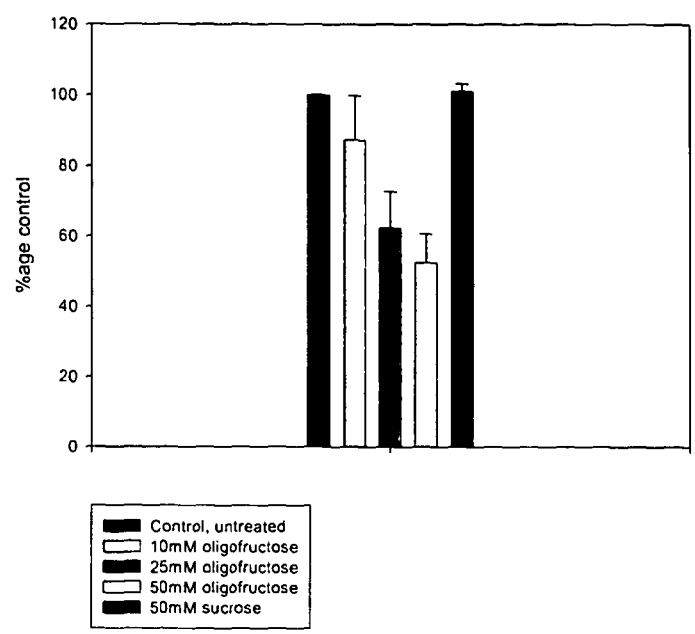
FIG. 5 shows the results of oligofructose in inhibiting keratinocyte proliferation.

The results for the oligosaccharide, oligofructose are shown in FIG. 5 and demonstrate that oligofructose, but not sucrose, inhibits keratinocyte proliferation. There were approximately 50% less cells in samples treated with oligofructose at the highest concentration tested compared with the controls.

It was also demonstrated that non-digestible oligosaccharide are not toxic to the cells at the concentrations used by testing confluent monolayers for LDH (Lactate dehydrogenase) release. LDH is an enzyme that is measured to show that cells are not damaged. The results are shown in FIG. 7 and show that no LDH release was detected over baseline levels for any non-digestible oligosaccharide (NDS) (for example, oligofructose) at any concentration used.

Conclusions

The data discussed above demonstrates that non-digestible oligosaccharides interact directly with model enterocytes leading to changes in their activity. Within five minutes of adding non-digestible oligosaccharides to caco-2 cells, an approximately 4-fold increase in the intensity of staining for PKC at the membrane over baseline was observed. Upon activation, PKC migrates to the plasma membrane where it interacts with other proteins usually by phosphorylating them. Therefore, movement to the membrane is a proxy for PKC activation. This suggests that non-digestible oligosaccharides can induce activation of PKC in caco-2 cells. Opening of tight junctions in caco-2 cells in response to non-digestible oligosaccharides was also observed. The first measurement was taken one hour post treatment and demonstrated that the TEER, a proxy for tight junction opening, had decreased to approximately 40% of baseline levels. By two hours, the TEER had reduced a little further. Later time points revealed no further reductions, suggesting that tight junction opening was maximal by two hours. The digestible saccharide, sucrose, did not open up tight junctions or induce PKC activation suggesting that these effects are specific to non-digestible oligosaccharides.

Figure 6:
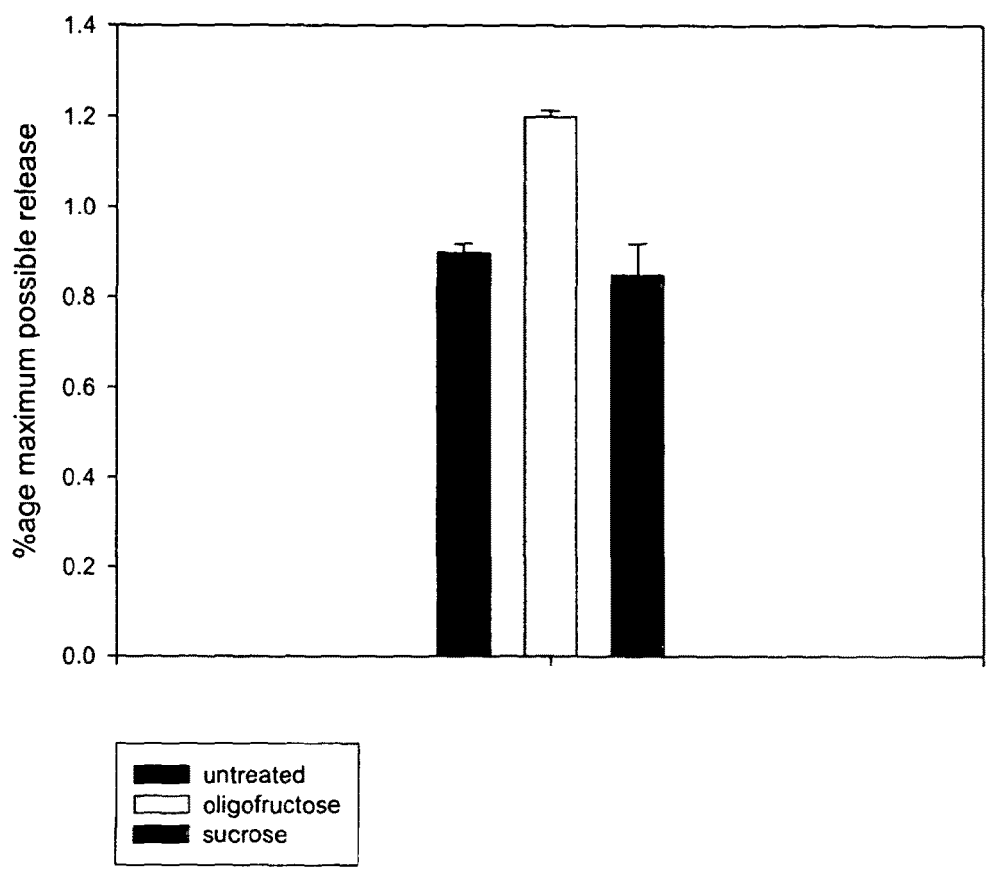
FIG. 6 shows the results of testing confluent monolayers for LDH release for control, oligofructose, and sucrose.

A significant reduction in cell number was observed in samples of epidermal keratinocytes treated with non-digestible oligosaccharides, but not sucrose. The non-digestible oligosaccharides were not toxic to the cells and it was therefore concluded that non-digestible oligosaccharides can inhibit cellular proliferation in keratinocytes. Effects on cellular proliferation were dose dependent, with more potent inhibition of proliferation with increasing concentration of non-digestible oligosaccharide (as shown in FIGS. 5 and 6).

The data suggests that non-digestible oligosaccharides can interact directly with both enterocytes and keratinocytes to alter basic cellular functions.

EXAMPLE 2

In order to investigate the direct effects of oligofructose on human skin, a fresh human skin ex vivo system is used. Over a culture period of 1, 2 and 3 weeks, oligofructose is applied to micro-dissected, full-thickness human skin fragments (3 mm punches of defined volume) obtained with the subjects informed consent from elective plastic surgery.

The edges of the skin fragments are in a (trauma-induced) hyper-proliferative state and facilitate anti-proliferative measurements using quantitative immuno-histomorphometry for the proliferation marker Ki67. This biomarker is used to assess the anti-proliferative effects of oligofructose. The apoptosis promoting effect of oligofructose on epidermal keratinocytes will be evaluated using the TUNEL assay which assay is conducted using a commercially available assay kit (as described in Gavrieli Y, Sherman Y, Ben-Sasson SA, J. Cell Biol., 1992, November, 119(3), 493-501).

Quantitative immunofluoresence is used to determine the effective dose of oligofructose for intraepithelial tight junction modulation. This provides mechanistic proof of principle for non-digestible oligosaccharide treatment and tight junction modulation. Histology demonstrates mid and long-term morphological changes induced following skin exposure.

A dose response profile will be established based on effectiveness; cell proliferation and cell death.

EXAMPLE 3

Clinical Study Plan.

For the clinical study a technique called the Scholtz-Dumas bioassay was used which is designed to assess whether substances applied to psoriatic plaques change their characteristics. In the study small amounts of creams were applied across a template containing different amounts of naturally-occurring non-digestible oligosaccharides onto small areas (approximately 2 $cm^2$) of patients' skin on 6 occasions over 14 days. Cream was also applied without the presence of non-digestible oligosaccharides and also cream which contained a mild steroid known to be effective against psoriasis as a control. Two sets of repeat applications were performed; one set covered (occluded) to maximise the penetration of the naturally-occurring chemical into the skin and the other set left uncovered.

The study was conducted in accordance with the Declaration of Helsinki and Good Clinical Practice. Local adult (greater than 18 years) patients with mild to moderate stable chronic plaque psoriasis were recruited. Exclusion criteria were; less than 18 years, pregnancy or lactation, liver disease, exposure to natural or artificial UVR, immunosuppression due to disease or medication. Disease severity and response to treatment was quantified using an established measure of clinical severity: psoriasis area severity index (PASI) and the dermatology life quality index DLQI which assesses disease impact on patients' quality of life. The plaque bioassay described by Scholtz and Dumas in which various concentrations of topical preparations are applied in Finn chambers under occlusion to individual plaques was used in an open, dose-ranging study (Katz et al, 2000). Assessment of the effect of topical preparations on symmetrical plaques was conducted using standard 0-12 composite score of erythema, induration and scaling (EIS). Skin barrier function of involved and non-involved skin areas was assessed using a Vapometer® which quantifies trans-epidermal water loss (TEWL) and skin pH was measured using an appropriate meter. Patients were asked to cease active psoriasis treatment during the study and use only non-UVB absorbing emollients. The statistical analyses were conducted by a medical statistician.

Clinical Study Plan

Groups 1: Open dose ranging study of topical preparations. After a two week wash-out period from active topical medications for psoriasis, a dose range of active in a cream was applied to small areas of an individual plaque under occlusion in a Scholtz-Dumas bioassay, every other day for a period of 12 days. At each clinic visit individual areas were scored using the EIS system.

Groups 2: Randomise, double-blind, placebo-controlled study of topical. After the two week wash-out period, patients randomised into group 2 were supplied with blinded, randomised topical formulations of placebo or active topical at two concentrations (informed by the Scholtz-Dumas study) in packaging marked either 'LEFT' or 'RIGHT'. Subjects applied topical test formulations onto identified, accessible, symmetrical plaques and to a 5 cm margin around each plaque once daily for a period of 8 weeks. Before, and at 4 weeks, and the end of study, plaque severity was scored using the EIS system. Plaques and margins were also assessed for skin pH and TEWL to determine the beneficial effects of topical active on psoriasis plaques.

Groups 3 & 4: Randomise, double-blind, placebo-controlled study of oral NDS. After the two week wash-out period, patients randomised into groups 3 and 4 were supplied with identically packaged capsule, tablet or powder form sachets of NDS or placebo which they were asked to ingest in a drink. Before and at every four weeks of the study measurements of PASI, DLQI, and skin pH and TEWL on involved and non-involved skin was conducted to determine the beneficial effects of oral treatment on disease severity and skin barrier function. Safety was assessed by physical examination and laboratory blood test including standard liver function tests (LFT), urea and electrolytes (U&E) and full blood count (FBC) at the start, at 1 month and the end of the treatment period. Table 1 below provides details of the clinical study plan.

TABLE 1

| Number (n) | PASI, TEWL | Weeks 1-2 Washout | PASI, TEWL | Weeks 3-6 | PASI, TEWL | Weeks 7-10 | PASI, TEWL | Weeks 11-14 | PASI, TEWL | Weeks 15-18 | PASI, TEWL |
|---|---|---|---|---|---|---|---|---|---|---|---|
| 1 (12) | ++ | PASI | ++ | Topical placebo to one forearm Topical active to one forearm | ++ | | | | | | |
| 2 (8) | ++ | PASI, TEWL | ++ | oral placebo | ++ | oral placebo PASI | ++ | oral active PASI | ++ | oral active PASI | ++ |
| 3 (8) | ++ | PASI, TEWL | ++ | oral active | ++ | oral active PASI | ++ | oral placebo PASI | ++ | oral placebo PASI | ++ |

Topical Non-Digestible Oligosaccharides; a Randomized, Double-Blind, Placebo Controlled Study.

Subjects were provided with topical formulations of either placebo or oligofructose. All subjects were advised to apply active and placebo topical formulations onto each of two symmetrical plaques once daily for four weeks. Over the study, plaques are monitored for EIS (standard grading system for Erythema, Induration and Scaling) and TEWL. Comparative measurements of EIS and skin TEWL on placebo versus active plaques determine the beneficial effects of topical oligofructose on disease and skin barrier function.

Oral Non-Digestible Oligosaccharides; a Randomized, Double-Blind, Placebo Controlled Study.

Subjects were provided with once a day sachets containing a fixed dose of either placebo or oligofructose. Subjects were asked to sprinkle the oligofructose on cereal or if preferred, dissolve it in water and take it as a drink. After eight weeks, the oral treatment crossed over so that patients taking placebo took active and vice versa. Every four weeks comparative disease PASI (Psoriasis Area Severity Index) scores and TEWL measurements were taken.

EXAMPLE 4

A typical ointment for topical administration may contain:

| Ingredient | % weight/weight |
|---|---|
| Oligofructose | 1.0 |
| Emusifying Ointment BP ™ (White Soft Paraffin, Liquid Paraffin, Emusifying Wax mixture) | 30.0 |
| Isopropyl Myristate | 5.0 |
| Hydroxyethylcellulose | 0.2 |
| Glycerol | 1.0 |
| Phenoxyethanol | 1.0 |
| Purified Water | 61.8 |

EXAMPLE 5

A typical ointment for topical administration may contain:

| Ingredient | % weight/weight |
|---|---|
| Oligofructose | 2.0 |
| Emusifying Ointment BP ™ (White Soft Paraffin, Liquid Paraffin, Emusifying Wax mixture) | 30.0 |
| Isopropyl Myristate | 5.0 |
| Hydroxyethylcellulose | 0.2 |
| Glycerol | 1.0 |
| Phenoxyethanol | 1.0 |
| Purified Water | 60.8 |

EXAMPLE 6

A typical ointment for topical administration may contain:

| Ingredient | % weight/weight |
|---|---|
| Oligofructose | 1.0 |
| Hydroxyethylcellulose | 2.0 |
| Propylene Glycol | 20.0 |
| Phenoxyethanol | 1.0 |
| Purified Water | 76.0 |

EXAMPLE 7

A typical ointment for topical administration may contain:

| | |
|---|---|
| Oligofructose | 2.5 g |
| Polyethylene glycol 1500 | 5.0 g |
| Polyethylene glycol 4000 | 15.0 g |
| Polyethylene glycol | 100.0 g |

EXAMPLE 8

A typical tablet, which may be prepared by conventional tableting techniques (for example by compression), may contain:

| Core: | |
|---|---|
| Oligofructose | 200 to 500 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | quantum sufficiat |
| Coating: | |
| Hydroxypropyl methylcellulose | about 9 mg |
| Mywacett ® 9-40 T** | about 0.9 mg |

*Polacrillin potassium NF, Tablet disintegrant, Rohm and Haas
**Acylated monoglyceride used as plasticizer for film coating
Lactosum Ph. Eur. is the monohydrate of 4-0-(β-D-Galactopyranosyl)-alpha-D-glucopyranose (Lactose monohydrate)

EXAMPLE 9

A nutritional product in the form of a free-flowing powder formulation (containing 5.0 g of oligofructose) that is suitable for packaging in a sachet was prepared. The powder mix may be diluted to taste and drunk when required by a subject suffering from a skin disorder The powder formulation was prepared by mixing 5.0 g of powdered oligofructose and 0.2 g of a standard spray-dried mix of flavouring.

EXAMPLE 10

A nutritional product in the form of a free-flowing powder formulation (containing 3.0 g of oligofructose) that is suitable for packaging in a sachet was prepared. The powder mix may be diluted to taste and drunk when required by a subject suffering from a skin disorder The powder formulation was prepared by mixing 3.0 g of spray-dried oligofructose with 0.5 g powdered citric acid, 26.3 g of granulated sugar and 0.2 g of a standard spray-dried mix of flavouring.

EXAMPLE 11

A nutritional product in the form of an orange drink (containing 3.0 g of oligofructose) was prepared as follows:
(a) 3.5 g of freeze-dried oligofructose (powder) was dissolved in 100 ml of orange juice (or alternatively with orange juice concentrate and water); or
(b) 2.5 g of freeze-dried oligofructose (powder) was dissolved in 100 ml of orange juice (or alternatively with orange juice concentrate and water).

The orange drink preparations (a or b) may be consumed by a subject immediately, refrigerated for later consumption or sealed in a bottle or carton for a longer shelf life. It will be appreciated that orange juice may be readily substituted with a palatable alternative.

The invention claimed is:

1. A method of producing an anti-proliferative effect in a subject suffering from psoriasis by limiting hyper-proliferation of keratinocytes in an affected area of the epidermis of the subject, the method comprising administering topically to the affected area of the subject a topical composition comprising a therapeutically effective amount of an anti-hyperproliferative agent or administering orally to the subject a composition comprising a therapeutically effective amount of an anti-hyperproliferative agent, wherein the anti-hyperproliferative agent consists of oligofructose or a salt thereof present in an amount of from 2.0 to 25% by weight of the total composition, said therapeutically effective amount being sufficient to limit hyperproliferation of keratinocytes in the epidermis of the subject.

2. The method according to claim 1 wherein the composition is formulated as a topical pharmaceutical composition.

3. The method according to claim 1 wherein the keratinocyte hyper-proliferation is plaque psoriasis keratinocyte hyper-proliferation.

4. The method according to claim 1 wherein the topical composition further comprises a pharmaceutically-acceptable diluent or carrier selected from the group consisting of: peanut oil, water, ethyl cocoate octyl cocoate, polyoxyethylenated hydrogenated caster oil, liquid paraffin, isopropanol, glycerol, propylene glycol, paraffin, cellulose, parabens, stearyl alcohol, polyethylene glycol, isopropyl myristate and phenoxyethanol.

5. The method according to claim 1 wherein the topical composition is selected from the group consisting of: solutions, creams, ointments, jellies, gels, shampoos, sprays, foams, powders, liposomes, aqueous solutions, oily solutions, and suspensions.

6. The method according to claim 1 wherein the anti-hyperproliferative agent is oligofructose.

7. A method of limiting hyperproliferation of keratinocytes in the epidermis of a subject suffering from psoriasis comprising using a topically applied composition comprising an antihyperproliferation agent which inhibits proliferation of keratinocytes when said keratinocytes are exposed to the anti-hyperproliferative agent in vitro, wherein the anti-hyperproliferative agent consists of oligofructose or a salt thereof present in an amount of from 2.0 to 25% by weight of the total composition.

8. A method according to claim 1 in which the anti-hyperproliferative agent inhibits proliferation of keratinocytes when said keratinocytes are exposed to the anti-hyperproliferative agent in vitro.

9. A method according to claim 1 which comprises administering topically to the affected area of the subject the topical composition comprising the therapeutically effective amount of the anti-hyperproliferative agent.

10. A method of producing an anti-proliferative effect in a subject suffering from psoriasis by limiting hyper-proliferation of keratinocytes in an affected area of the epidermis of the subject, the method comprising administering topically to the affected area of the subject a topical composition comprising a therapeutically effective amount of an anti-hyperproliferative agent or administering orally to the subject a composition comprising a therapeutically effective amount of an anti-hyperproliferative agent, wherein the anti-hyperproliferative agent consists of oligofructose or a salt thereof present in an amount of from 2.0 to 25% by weight of the total composition, said therapeutically effective amount being sufficient to limit hyperproliferation of keratinocytes in the epidermis of the subject, said oligofructose being produced from a natural source by enzymatic hydrolysis.

* * * * *